(12) United States Patent
Soliman

(10) Patent No.: US 12,060,530 B2
(45) Date of Patent: Aug. 13, 2024

(54) PROCESS CONTROL SYSTEMS AND METHODS FOR SIMULTANEOUS CRUDE OIL DEHYDRATION, DESALTING, SWEETENING, AND STABILIZATION

(71) Applicant: Saudi Arabian Oil Company, Dhahran (SA)

(72) Inventor: Mohamed Soliman, Ras Tanura (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 18/352,420

(22) Filed: Jul. 14, 2023

(65) Prior Publication Data

US 2023/0357651 A1   Nov. 9, 2023

Related U.S. Application Data

(62) Division of application No. 17/330,091, filed on May 25, 2021, now Pat. No. 11,760,946.

(51) Int. Cl.
  *C10G 53/02* (2006.01)
  *B01D 17/02* (2006.01)
  (Continued)

(52) U.S. Cl.
  CPC ......... *C10G 53/02* (2013.01); *B01D 17/0214* (2013.01); *B01D 17/06* (2013.01); *B01D 17/12* (2013.01); *C02F 1/40* (2013.01); *G01N 33/2847* (2013.01); *G01R 19/0046* (2013.01); *G05D 9/12* (2013.01); *C02F 2101/32* (2013.01); *C10G 2300/208* (2013.01)

(58) Field of Classification Search
  None
  See application file for complete search history.

(56) References Cited

U.S. PATENT DOCUMENTS 4,209,695 A   6/1980   Arnold et al.
4,352,288 A   10/1982  Paap et al.
(Continued)

OTHER PUBLICATIONS

Alshehri et al. "Designing and Testing a Chemical Demulsifier Dosage Controller in a Crude Oil Desalting Plant: An Artificial Intelligence-Based Network Approach", Chemical Engineering Technology, 2010, 33, No. 6, pp. 973-982.

*Primary Examiner* — Tam M Nguyen
(74) *Attorney, Agent, or Firm* — Bracewell LLP; Constance G. Rhebergen; Eleanor T. Porter

(57) ABSTRACT

Systems and methods for controlling desalting and dehydration of crude oil, one method including monitoring total dissolved solids (TDS) content at an outlet stream from a crude oil separation unit, the outlet stream comprising water; monitoring basic sediment and water (BS&W) content at an outlet stream from the crude oil separation unit, the outlet stream comprising processed crude oil; determining pounds per thousand barrels (PTB) salt content and volumetric water content of a dried, desalted crude oil product stream using the TDS content and BS&W content; and controlling a process input to the method from a comparison between the PTB salt content and volumetric water content of the dried, desalted crude oil product stream versus a maximum set value for PTB salt content and volumetric water content of the dried, desalted crude oil product stream.

15 Claims, 7 Drawing Sheets

(51) Int. Cl.
*B01D 17/06* (2006.01)
*B01D 17/12* (2006.01)
*C02F 1/40* (2023.01)
*G01N 33/28* (2006.01)
*G01R 19/00* (2006.01)
*G05D 9/12* (2006.01)
*C02F 101/32* (2006.01)

(56) References Cited

U.S. PATENT DOCUMENTS

| | | | |
|---|---|---|---|
| 4,581,134 | A | 4/1986 | Richter, Jr. et al. |
| 5,332,900 | A | 7/1994 | Witzke et al. |
| 6,831,470 | B2 | 12/2004 | Xie et al. |
| 7,927,479 | B2 | 4/2011 | Greaney et al. |
| 9,181,499 | B2 | 11/2015 | Mason et al. |
| 10,023,811 | B2 | 7/2018 | Soliman et al. |
| 10,260,010 | B2 | 4/2019 | Soliman |
| 10,370,599 | B2 | 8/2019 | Salu et al. |
| 10,429,858 | B2 | 10/2019 | Prasad et al. |
| 10,513,663 | B2 | 12/2019 | Soliman et al. |
| 10,703,987 | B2 | 7/2020 | Al Seraihi et al. |
| 2010/0310877 | A1* | 12/2010 | Parker .................. C09J 189/00 252/182.28 |
| 2014/0131254 | A1 | 5/2014 | Soliman |
| 2017/0254793 | A1 | 9/2017 | Al-Amri |
| 2021/0107817 | A1 | 4/2021 | Kantani et al. |
| 2022/0380688 | A1* | 12/2022 | Soliman .................. C02F 1/008 |
| 2022/0402781 | A1 | 12/2022 | Soliman |

\* cited by examiner

PROCESS CONTROL SYSTEMS AND METHODS FOR SIMULTANEOUS CRUDE OIL DEHYDRATION, DESALTING, SWEETENING, AND STABILIZATION

CROSS-REFERENCE TO RELATED APPLICATIONS

This patent application is a divisional of U.S. Non-Provisional patent application Ser. No. 17/330,091 filed on May 25, 2021. For purposes of United States patent practice, the non-provisional application is incorporated by reference in its entirety.

BACKGROUND

Field

The present disclosure relates to gas oil separation plant (GOSP) technology. In particular, the disclosure relates to integrated process control for crude oil desalting, dehydration, sweetening, and stabilization to create efficient GOSP systems and processes to aid in crude oil separations.

Description of Related Art

In general, a GOSP is a continuous separation process used to refine crude oil that includes a high pressure production trap (HPPT), a low pressure production trap (LPPT), a low pressure degassing tank (LPDT), a dehydrator unit, first and second stage desalting units, a water/oil separation plant (WOSEP), a stabilizer column, centrifugal pumps, heat exchangers, and reboilers. In a GOSP, the pressure is often reduced in several stages to allow the controlled separation of volatile components, such as entrained vapors. Goals of a GOSP include achieving maximum liquid recovery with stabilized oil separated from gas, and water separated from gases and oil. In other words, one purpose of a GOSP is to remove water, salt, and volatile hydrocarbon gases from wet crude oil after it is obtained from a hydrocarbon-bearing reservoir.

However, a large pressure reduction in a single separator will cause flash vaporization, leading to instability and safety hazards. Thus, in prior art GOSP's, many stages and units are required, as described in U.S. Pat. Nos. 10,260,010 and 10,023,811, incorporated herein by reference in their entirety. In a first stage, gas, crude oil, and free water are separated. In a second stage, crude oil is dehydrated and desalted to separate emulsified water and salt to meet certain basic sediment and water (BS&W) specifications. In a third stage, crude oil is stabilized and sweetened to meet hydrogen sulfide ($H_2S$) and Reid Vapor Pressure (RVP) specifications.

GOSP's are oftentimes operated to meet the following specifications: (1) a salt concentration of not more than about 10 pounds (lbs.) of salt/1000 barrels (PTB); (2) BS&W content of not more than about 0.3 volume percent (V %); (3) $H_2S$ content (concentration) of less than about 60 ppm in either the crude stabilization tower (or degassing vessels in the case of sweet crude not requiring stabilization); and (4) a maximum RVP of about 7 pounds per square inch absolute (psia) and a maximum true vapor pressure (TVP) of about 13.5 psia at 130 degrees Fahrenheit (° F.).

Currently, there is no effective and inexpensive application of online analyzers for real-time monitoring of salt content in treated crude oil. Available online salt-in-crude analyzers are generally expensive and require frequent maintenance, along with the use of solvents. Xylene and alcohols are generally added to treated crude samples in measurable quantities, and the conductivity is measured, which is proportional to the salt content. The frequent replacement of chemicals and the presence of moving parts in the analyzers makes the analyzers labor-intensive, and the analyzers require frequent maintenance. Online nuclear and radioactive-based salt-in-crude analyzers also require frequent, expensive maintenance and measurements are generally unreliable. Due to these deficiencies, off-spec crude in between salt-in-crude measurements is common. Therefore, reliable, real-time, online measurements are needed in GOSP systems and methods for control to reach required dehydration and salt-in-crude specifications.

SUMMARY

The present disclosure describes integrated GOSP systems and processes with unique process control strategies to meet crude oil export specifications and use less processing units than prior art GOSP's. Disclosed embodiments provide robust process control strategies to continuously measure and control the salinity (salt-in-crude content) of one or more dry crude oil stream exiting a crude oil separation unit, such as a desalter or dehydrator, in a GOSP or refinery using innovative and reliable oil-water emulsion interface level management. Online, real-time measurements of salt-in-crude content can be used to control and optimize wet crude handling units to meet the export dry crude specification of 10 lbs. of salt per 1000 barrel of dry crude (PTB) at minimum cost. Systems and methods of the present disclosure can achieve crude oil export specifications including: (1) a salt concentration of not more than about 10 PTB; (2) BS&W content of not more than about 0.3 V %; (3) $H_2S$ content of less than about 60 ppmw in either the crude stabilization tower (or degassing vessels in the case of sweet crude not requiring a stabilization tower); and (4) a maximum RVP of about 7 psia and a maximum TVP of about 13.5 psia at 130° F.

Embodiments of systems and methods of the disclosure provide the ability to separate and stabilize crude oils with "tight" emulsions and increased water cuts that existing GOSP systems and methods cannot separate and stabilize. In other words, conventional desalters can treat crude oils with a water cut between about 30% and about 35% by volume. However, embodiments of the present disclosure efficiently treat crude oils to remove water when the water cut is greater than about 35%. Tight emulsion crude oil normally occurs in medium to heavy crude oils with American Petroleum Institute ("API") numbers less than about 29. Oil specific gravity in the API scale is typically used as a measure of oil quality. A greater API value indicates a lighter oil and, thus, a greater market value.

Water cut in oil production refers to the total volume of water in the crude oil stream divided by the total volume of crude oil and water. In other words, water cut percent is equal to the total volumetric flowrate of water divided by the volumetric flowrate of water and oil multiplied by 100. Water cut generally increases with the age of an oil well. For example, water cut at the beginning of the life of a well is around zero percent, but as the well ages, water cut can reach close to 100%.

In certain embodiments, systems and methods are provided to treat wet and sour, unstabilized crude oil to meet shipping and transport specifications by simultaneously dehydrating, desalting, stabilizing, and sweetening the crude oil. In some embodiments, three conventional stages of processing crude oil will be done in only one stage, system, or process. In some embodiments, crude oil desalting, dehydration, sweetening, and stabilization will be integrated within existing three phase separation vessels within a GOSP along with gas compression and gas recycle for heating. Dehydrating crude oil involves the separation of formation water, while desalting includes washing the crude with fresh water in addition to or alternative to recycle water to meet the required salt content and BS&W. Recycled water can be used in disclosed systems and methods to reduce the amount of fresh wash water required.

Crude sweetening involves the removal of dissolved $H_2S$ from crude oil to meet specifications in a range of about 10-60 ppmw, while crude stabilization involves the removal of light ends from crude oil, mainly $C_1$-$C_4$ hydrocarbons to reduce the TVP to less than about 13 psia at 130° F. below atmospheric pressure, or in other words no vapor will flash under atmospheric conditions, making it safe for transportation and shipment. Stabilizing the crude can be achieved if crude is heated in multiple stages of separation drums working at increasing temperatures and reduced pressure.

In some embodiments, crude oil components can be separated in a series of separation vessels in which off-gases are removed from the separation vessels and compressed to heat incoming crude oil to enhance the separation, in particular focusing on systems and processes with 3-phase separation vessels including fully insulated electrostatic electrodes. In some embodiments the advantages of the systems and processes include eliminating certain existing crude oil stabilizer columns, eliminating crude oil stabilizer reboilers, eliminating crude oil charge pumps, eliminating $1^{st}$ and/or $2^{nd}$ stage desalters, and eliminating separate crude oil dehydrators. Systems and processes are compact and easily mobilized for deployment in small scale and offshore rig applications. Energy savings and efficiency can be increased by separating water before heating in a HPPT.

Therefore, disclosed herein are integrated gas oil separation plant systems and methods with integrated process control, one method for controlling desalting of crude oil including monitoring total dissolved solids (TDS) content at an outlet stream from a crude oil separation unit, the outlet stream comprising water; monitoring basic sediment and water (BS&W) content at an outlet stream from the crude oil separation unit, the outlet stream comprising processed crude oil; determining pounds per thousand barrels (PTB) salt content and volumetric water content of a dried, desalted crude oil product stream using the TDS content and BS&W content; and controlling a process input to the method from a comparison between the PTB salt content and volumetric water content of the dried, desalted crude oil product stream versus a maximum set value for PTB salt content and volumetric water content of the dried, desalted crude oil product stream. In some embodiments, the outlet stream comprising water comprises a bottoms stream from a water-oil emulsion separation unit. In other embodiments, the outlet stream comprising processed crude oil comprises a top product stream from a water-oil emulsion separation unit. Still in other embodiments, the step of determining the PTB salt content comprises applying Equation 1 with the TDS content and BS&W content. In yet other embodiments, the method includes the step of monitoring current and voltage supplied to an electric grid of the crude oil separation unit to control removal of an oil-water emulsion proximate an oil-water interface of the crude oil separation unit.

Still other embodiments of the method include the step of monitoring current and voltage supplied to the electric grid of the crude oil separation unit to control removal of water via a water drain of the crude oil separation unit. In some embodiments, when electric current supplied to the electric grid is at between 0% to about 50% of a set, maximum current value, removal of the oil-water emulsion proximate the oil-water interface of the crude oil separation unit proceeds for recycle of the oil-water emulsion to the crude oil separation unit. In other embodiments, when electric current supplied to the electric grid is at between about 50% to about 100% of a set, maximum current value, removal of water via the water drain of the crude oil separation unit proceeds. Still other embodiments of the method include the steps of monitoring the water level of the crude oil separation unit or the oil-water emulsion level of the crude oil separation unit and controlling the water drain of the crude oil separation unit using the monitored water level or monitored emulsion level.

In yet other embodiments, the maximum set value for PTB salt content is about 10 PTB and the maximum set value for volumetric water content is about 0.3 volume percent for the dried, desalted crude oil product stream. Still in other embodiments, the controlled process input to the method includes a process input selected from the group consisting of: chemical demulsifier injection rate; wash water injection rate; inlet crude oil heating; a pressure drop for mixing preceding the crude oil separation unit; current supply to the crude oil separation unit; inlet crude oil flow rate for processing; outlet crude oil flow rate of the dried, desalted crude oil product stream; crude oil separation unit residence time; crude oil separation unit emulsion level; crude oil separation unit water level; and combinations thereof.

Still in other embodiments, the step of controlling includes the application of a controller selected from the group consisting of: a distributed control system; a multi-variable controller; a multivariable predictive controller; and combinations thereof. Other embodiments of the method include the steps of monitoring water content and TDS of inlet crude oil for processing in the crude oil separation unit. Still other embodiments include the step of monitoring current and voltage supplied to an electric grid of an inline electrostatic emulsion breaker unit. In some embodiments, when electric current supplied to the electric grid of the inline electrostatic emulsion breaker is at between 0% to about 50% of a set, maximum current value, removal of an oil-water emulsion proximate an oil-water interface of the crude oil separation unit proceeds for recycle of the oil-water emulsion to the crude oil separation unit through the inline electrostatic emulsion breaker.

In still other embodiments, when electric current supplied to the electric grid of the inline electrostatic emulsion breaker is at between about 50% to about 100% of a set, maximum current value, removal of water via a water drain of the crude oil separation unit proceeds. In other embodiments, the method includes the step of monitoring BS&W content at an inlet of the inline electrostatic emulsion breaker. In some embodiments, the step of monitoring TDS content comprises monitoring TDS content following a first stage desalter and a second stage desalter, wherein the step of monitoring BS&W content comprises monitoring BS&W content following the first stage desalter and the second stage desalter, and wherein the step of determining PTB salt content and volumetric water content of the dried, desalted crude oil product occurs following both the first stage desalter and second stage desalter.

Other embodiments include the steps of recycling an emulsion layer from the first stage desalter through a first inline electrostatic emulsion breaker back to the first stage desalter and recycling an emulsion layer from the second stage desalter through a second inline electrostatic emulsion breaker back to the first stage desalter. Other embodiments include the steps of monitoring the current and voltage supplied to the first stage desalter, second stage desalter, first inline electrostatic emulsion breaker, and second stage inline emulsion breaker to control the recycle of the emulsion layers and to control water drained from the first stage desalter and second stage desalter via a water drain.

Additionally disclosed are systems for controlling desalting of crude oil, one system including a crude oil separation unit, the crude oil separation unit comprising a crude oil inlet, insulated electrostatic electrodes, a water outlet, an oil-water emulsion outlet, and a dried, desalted crude oil product outlet; a total dissolved solids (TDS) content monitor at the water outlet; a basic sediment and water (BS&W) content monitor at the dried, desalted crude oil product outlet; and a pounds per thousand barrels (PTB) salt content and volumetric water content controller in electronic communication with the TDS content monitor and the BS&W content monitor, wherein the PTB salt content and volumetric water content controller controls a process input to the system from a comparison between the PTB salt content and volumetric water content of the dried, desalted crude oil product outlet versus a maximum set value for PTB salt content and volumetric water content of the dried, desalted crude oil outlet.

In some embodiments, the PTB salt content and volumetric water content controller applies Equation 1 with on-line, real-time TDS measurements from the TDS content monitor and on-line, real-time BS&W measurements from the BS&W content monitor. In other embodiments, the systems include a current monitor and a voltage monitor for the insulated electrostatic electrodes, the current monitor and voltage monitor in electronic communication with a current controller, where the current controller is operable to control removal of water via the water outlet and removal of an oil-water emulsion via the oil-water emulsion outlet. In yet other embodiments the systems include a flow controller, the flow controller in electronic communication with the current controller and in electronic communication with a level controller of the crude oil separation unit, the level controller operable to measure a water level or oil-water emulsion level in the crude oil separation unit, and the flow controller operable to control water drained from the system via the water outlet.

In some embodiments, when electric current supplied to the insulated electrostatic electrodes is at between 0% to about 50% of a set, maximum current value, removal of the oil-water emulsion proximate an oil-water interface of the crude oil separation unit proceeds for recycle of the oil-water emulsion to the crude oil separation unit. In other embodiments, when electric current supplied to the insulated electrostatic electrodes is at between about 50% to about 100% of a set, maximum current value, removal of water from the system via a water drain following the water outlet proceeds. In yet other embodiments, the maximum set value for PTB salt content is about 10 PTB and the maximum set value for volumetric water content is about 0.3 volume percent for the dried, desalted crude oil product stream. Still in other embodiments, the controlled process input to the system includes a process input selected from the group consisting of: chemical demulsifier injection rate; wash water injection rate; inlet crude oil heating; a pressure drop for mixing preceding the crude oil separation unit; current supply to the crude oil separation unit; inlet crude oil flow rate for processing; outlet crude oil flow rate of the dried, desalted crude oil product outlet; crude oil separation unit residence time; crude oil separation unit emulsion level; crude oil separation unit water level; and combinations thereof.

In yet other embodiments, the system includes a controller selected from the group consisting of: a distributed control system; a multivariable controller; a multivariable predictive controller; and combinations thereof. In some embodiments, the controller is in one-way or two-way electronic communication with any one of or any combination of a chemical demulsifier injection control valve, a water content monitor for inlet crude oil, a total dissolved solids content monitor for inlet crude oil, a wash water injection control valve, a temperature indicator and control for crude oil inlet heating, a differential pressure indicator and control for control of a mixing valve for inlet crude oil, a current monitor for the insulated electrostatic electrodes, a voltage monitor for the insulated electrostatic electrodes, a level indicator and controller for a water level or oil-water emulsion level in the crude oil separation unit, the TDS content monitor at the water outlet, the BS&W content monitor at the dried, desalted crude oil product outlet, the PTB salt content and volumetric water content controller, a flow controller for draining water at the water outlet, a current controller in electronic communication with the current monitor for the insulated electrostatic electrodes and the voltage monitor for the insulated electrostatic electrodes, a current monitor for an inline electrostatic emulsion breaker, a voltage monitor for the inline electrostatic emulsion breaker, a current controller in electronic communication with the current monitor for the inline electrostatic emulsion breaker and the voltage monitor for the inline electrostatic emulsion breaker, and a BS&W content monitor at the oil-water emulsion outlet.

In still other embodiments, the systems include an inline electrostatic emulsion breaker at the oil-water emulsion outlet, the inline electrostatic emulsion breaker comprising a current monitor and voltage monitor in electronic communication with an inline electrostatic emulsion breaker current controller, the inline electrostatic emulsion breaker current controller operable to control an inlet valve to the inline electrostatic emulsion breaker. In some embodiments, when electric current supplied to an electric grid of the inline electrostatic emulsion breaker is at between 0% to about 50% of a set, maximum current value, removal of an oil-water emulsion proximate the oil-water emulsion outlet of the crude oil separation unit proceeds for recycle of the oil-water emulsion to the crude oil separation unit through the inline electrostatic emulsion breaker. Still in other embodiments, when electric current supplied to the electric grid of the inline electrostatic emulsion breaker is at between about 50% to about 100% of a set, maximum current value, removal of water via a water drain of the crude oil separation unit following the water outlet proceeds. In yet other embodiments, the systems include a BS&W content monitor at an inlet of the inline electrostatic emulsion breaker. In some embodiments, the crude oil separation unit comprises a first stage desalter and a second stage desalter. In still other embodiments, the first stage desalter recycles an emulsion layer to a first inline electrostatic emulsion breaker and where the second stage desalter recycles an emulsion layer to a second inline electrostatic emulsion breaker.

BRIEF DESCRIPTION OF THE DRAWINGS

These and other features, aspects, and advantages of the disclosure will become better understood with regard to the following descriptions, claims, and accompanying draw

DETAILED DESCRIPTION

Figure 1:
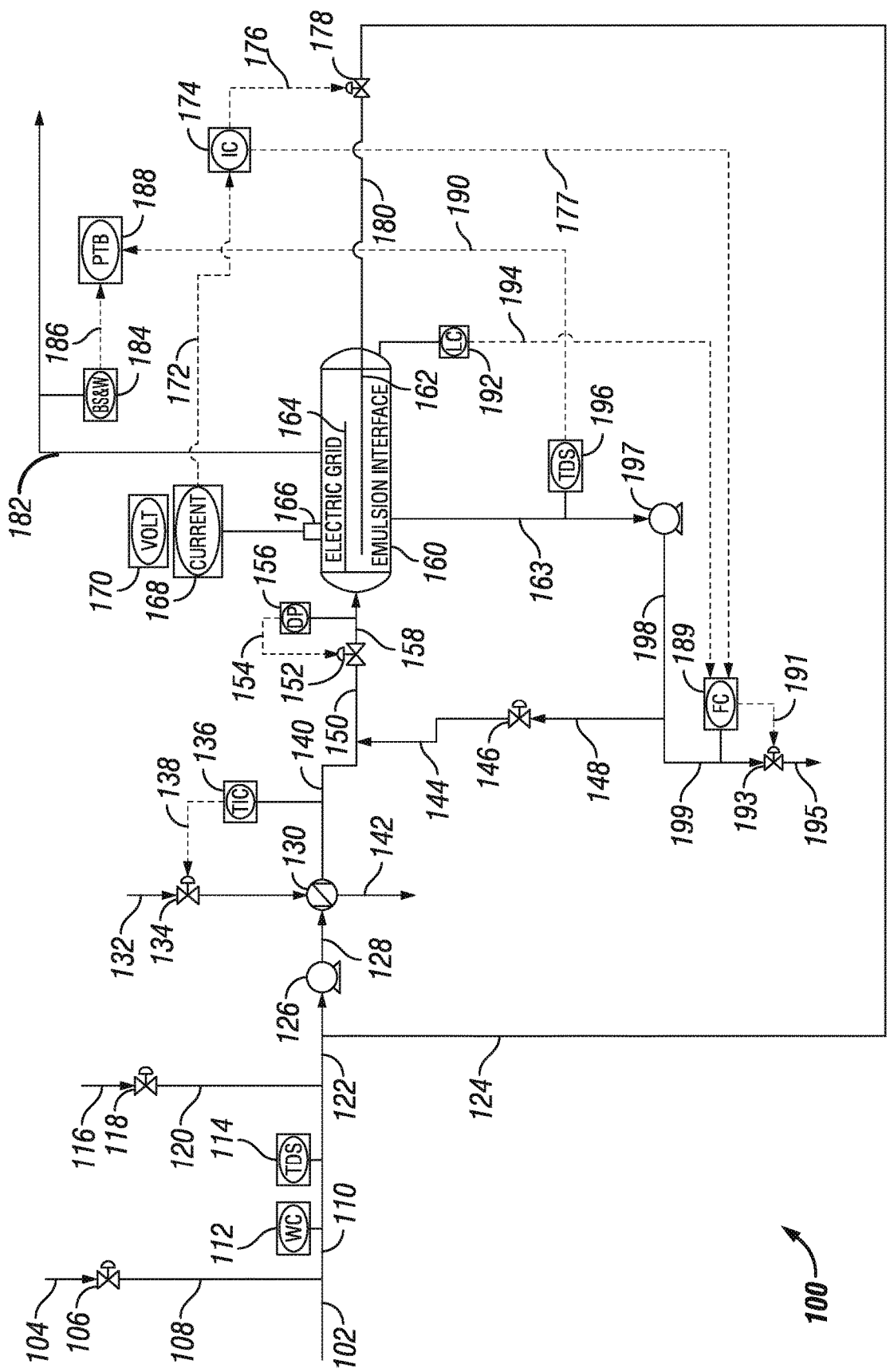
- FIG. 1 is a schematic diagram showing an integrated GOSP of the present disclosure with real-time process control for controlling salt-in-crude content and water content of produced dry crude oil.

While the disclosure will be described in connection with several embodiments, it will be understood that it is not intended to limit the disclosure to those embodiments. On the contrary, it is intended to cover all the alternatives, modifications, and equivalents as may be included within the spirit and scope of the disclosure defined by the appended claims.

Conventional GOSP's suffer from many deficiencies including low product yield, inefficient use of available heat sources such as for example the discharge streams of compressors, many separate units being used to meet product specifications, high operating costs due to heating requirements, a large spatial footprint, and high capital cost.

In general, a GOSP is a continuous separation system and process that includes a high pressure production trap (HPPT), a low pressure production trap (LPPT), a low pressure degassing tank (LPDT), a dehydrator unit, first and second stage desalting units, a water/oil separation plant (WOSEP), a stabilizer column, atmospheric compressors, low pressure compressors, high pressure compressors, centrifugal pumps, heat exchangers, and reboilers. In a conventional GOSP, pressure is often reduced in several stages to allow for the controlled separation of volatile components. Objectives of a GOSP include achieving maximum liquid recovery of stabilized oil and water, and gas separation. However, a large pressure reduction in a single separator will cause flash vaporization, leading to instability and safety hazards. In the embodiments of the figures described here, other units not pictured such as those described supra can be applied, depending on the quality of inlet crude oil and other factors. For example, a stabilizer column and stripping gas can be applied for crude oil with high sulfur content.

Prior art GOSP systems and processes generally include 3 separate stages in large-footprint plants and processes. In a first stage, gas, crude oil, and free water are separated. In a second stage, crude oil is dehydrated and desalted to separate emulsified water and salt to meet certain basic sediment and water (BS&W) specifications. In a third stage, crude oil is stabilized and sweetened to meet hydrogen sulfide ($H_2S$) and Reid Vapor Pressure (RVP) specifications. Generally, sour crude oil refers to any crude oil with a total sulfur level of more than about 0.5% by weight. In upstream operations, as described herein, the phrase sour crude also refers to any crude oil with an $H_2S$ content higher than about 60 ppm by weight, and sweet crude oil refers to any crude oil that has an $H_2S$ content of less than about 60 ppm by weight.

After stabilization and sweetening, the crude oil should meet all specifications required for shipment, transport, and storage. These specifications include the following: (1) a salt concentration of not more than about 10 PTB; (2) BS&W of not more than about 0.3 V %; (3) $H_2S$ content of less than about 60 ppm in the crude stabilization tower (or degassing vessels in the case of sweet crude); and (4) a maximum RVP of about 7 psia and a maximum TVP of about 13.5 psia at 130° F.

In embodiments of the present disclosure, high pressure off-gases and high pressure compressed gases are in a pressure range from about 150 psig or about 170 psig to about 460 psig, low pressure off-gases and low pressure compressed gases are in a pressure range from about 50 psig or about 70 psig to about 160 psig, and atmospheric pressure off-gases and atmospheric pressure compressed gases are in a range from about 3 psig to about 60 psig. The temperature of the off-gases depends, in part, on the source of the crude oil. For example, the initial temperature for crude oil originating from offshore oil rigs ranges between about 55° F. to about 100° F., while the temperature of crude oil originating from onshore oil fields ranges from about 100° F. to about 150° F. For example, in one embodiment the temperature of high pressure off-gas from an HPPT is about 95° F., the temperature of low pressure off-gas from a LPPT is about 95° F. (with no heater preceding the LPPT), and the temperature of the atmospheric pressure off-gas from a LPDT is about 125° F., due to a heater (heat exchanger) preceding the LPDT. One or more HPPT, LPPT, and/or LPDT can precede the systems described here, and one or more stabilization tower can follow, with stripping gas applied as needed in any of the vessels described to reduce sulfur content.

In some embodiments of the present disclosure, the operating temperatures of a HPPT and LPPT are substantially the same when no heater (heat exchanger) precedes the units. In some embodiments, the operating pressure of the HPPT is about 150 psig, the operating pressure of the LPPT is about 50 psig, and the operating pressure of the LPDT is about 3 psig. In some embodiments, the operating temperatures of the HPPT and LPPT are about 95° F., while the operating temperature of the LPDT is about 125° F.

In embodiments of the present disclosure, process control of a GOSP can be advantageously achieved with the addition of one or more unique basic sediment and water (BS&W) measurement devices or analyzers, for example placed to measure the BS&W content of a dry crude stream exiting a crude oil separation unit, such as a desalter or dehydrator. This allows measurement of BS&W content in volume percent, which for a dry crude stream exiting a desalter largely provides a measurement in volume percent of water volume versus the total crude volume. The "sediment" volume portion of the measure is negligible in most processed crude oils. In addition, one or more total dissolved solids (TDS) analyzer is placed to measure or analyze the TDS of a stream comprising water stream exiting a desalter or dehydrator. TDS measurements can be made by conductivity meters on a water stream exiting a desalter, for example a first stage desalter or second stage desalter, and TDS can be provided in a measurement of mg/liter, discussed further with regard to FIG. 1.

From uniquely placed BS&W and TDS analyzers in a GOSP, for example proximate one or more desalter or dehydrator, salt-in-crude content in PTB can be continuously calculated, monitored, and analyzed in real-time, for example according to Equation 1:

$$PTB = \frac{0.35}{\eta_{mix}} * \frac{BS \& W}{(100 - BS \& W)} * \left[1 + 0.695 * 10^{-6} * TDS\right] * TDS. \quad \text{(Eq. 1)}$$

In Equation 1, PTB is the PTB value in pounds of salt per one thousand barrels of a dry crude stream proceeding out from a desalter vessel or a dehydrator vessel; BS&W is the dry and processed crude basic sediment and water measurement in volume percent; TDS is an effluent water dissolved solids measurement in mg/L of the effluent water exiting from a desalter or a dehydrator; and $\eta_{mix}$ is the mixing efficiency to account for mixing inefficiencies due mixing valves, vessels, and the existence of solid salt crystals in crude oil. The PTB of the dry crude can be calculated as a function of the measurements of TDS and BS&W. In some embodiments, a typical value for $\eta_{mix}$ is 1.0 for 100% mixing efficiency, where all salts are dissolved in water, and the effluent water is the same as the water droplets suspended within the crude. The $\eta_{mix}$ value can be determined during the actual operation of the desalter or dehydrator to account for the actual mixing efficiency of the water droplets with salt and crude oil. For example, with a $\eta_{mix}$ of 1, a TDS of 28000 mg/l, and BSW of 0.1, the PTB is 10.

BS&W is the basic sediment and water content of a dry crude oil stream in volume percent exiting a crude oil separation unit, such as a desalter or dehydrator, where the suspended solids content is neglected because of the significantly low volume amount of sediment in dry crude oil exiting from a desalter or dehydrator, where BS&W content is substantially water, for example more than 90 volume percent or more than 95 volume percent water and less than 10 volume percent or less than 5 volume percent sediment. In other words, BS&W monitoring largely provides the volume percent of water in a crude oil stream. TDS in Equation 1 is the total dissolved solids in mg/liter or parts per million weight (ppmw) of a stream comprising water exiting a crude oil separation unit, such as a desalter or dehydrator.

Via uniquely placed devices for measurement, analysis, and/or monitoring in real-time proximate one or more desalter or dehydrator, desalter and dehydrator operation can be automated to meet the PTB specification maximum of 10 lbs./1000 barrel and BS&W specification maximum of 0.2 or 0.3 volume percent. Currently in desalter operations, there are substantial losses in chemical demulsifier and wash water, due to over injection, and also wasted energy due to over application of power to units such as insulated electrostatic electrodes. Additionally, off-spec crude for PTB is produced due to the lack of reliable PTB measurement and desalter automation. Currently, in systems and methods using manual control to meet the maximum salt content of 10 PTB and maximum water content of 0.2 V % or 0.3 V %, normal practices include operating at much lower than the specification maximum, for example at 5 PTB and 0.1 BS&W to avoid off-spec product. By utilizing embodiments of the present disclosure with the proposed advanced process controls, the specification limits can be more closely approached and systems and methods operated at the specification borderline of about 10 PTB and about 0.2 to about 0.3 V % BS&W without violating the specification maximum.

Certain surprising and unexpected benefits of embodiments of the present disclosure include: (1) real-time online monitoring of and continuous control of dry crude salt-in-crude content; (2) meeting dry crude product specifications, for example maximum of about 10 PTB, without waiting for separate laboratory test results; (3) saved laboratory sampling time and cost; (4) minimization of use of desalter wash water; (5) minimization of chemical demulsifier injection; (6) minimization in energy consumption of process pumps including wash water pumps (via minimization of wash water flow requirements), crude charge pumps (via optimization of mixing valve differential pressure), desalter wash water recycle pumps (via minimization of recycle wash water flow requirements), dehydrator recycle pumps (via minimization of dehydrator recycle flow requirements); (7) minimization of dehydrator power consumption; (8) minimization of desalter power consumption; (9) reduced man-hours spent physically collecting and analyzing crude samples and other samples from a GOSP; and (10) reduced corrosion rates to process equipment such as desalters and catalysts via control of salt-in-crude content.

To implement systems, processes, and methods of the present disclosure, one or more TDS conductivity meter can be installed and calibrated on a water outlet stream exiting from a desalter or dehydrator, for example a Pt stage and/or $2^{nd}$ stage desalter, and one or more BS&W analyzer can be installed and calibrated on a dry crude oil stream exiting from a desalter or dehydrator, for example a $1^{st}$ stage and/or $2^{nd}$ stage desalter. PTB measurements can calculated in a controller and/or distributed control system (DCS) according to Equation 1 based on real-time, online TDS and BS&W measurements, where set process variables can include any one of or any combination of PTB, TDS, and BS&W, and manipulated process variables include any one of or any combination of chemical demulsifier injection rate, wash water (fresh or recycle) injection rate, power consumption, water level in a crude oil separation vessel, oil-water emulsion level in a crude oil separation vessel, and pressure drop across valves for mixing.

A distributed control system (DCS) includes a computerized control system for a process or plant, optionally with more than one control loop, in which autonomous controllers are distributed throughout the system, but there is no central operator supervisory control required. Non-DCS systems include centralized controllers; either discrete controllers located at a central control room or within a central computer. DCS systems increase reliability and reduce installation costs by localizing control functions near a process or system, with remote monitoring and supervision.

Prior art oil refineries and GOSP's have not used PTB as a control variable based on readings from BS&W and TDS conductivity meters to control process units, such as desalters and dehydrators, to advantageously automate and optimize oil refinery and GOSP systems and processes. By calculating, controlling, and monitoring PTB in real-time via BS&W and TDS measurements, desalter and overall systems are optimized, and controlling salt-in-crude content via the disclosed embodiments enables the process of multivariable process control (MPC) for proper handling of wet, unprocessed crude oils. Process dependency on expensive, unreliable oil-water interface level measurements can be eliminated. Inexpensive, commercially-available BS&W and TDS measurement devices/analyzers can be placed to control PTB as a variable in real-time while avoiding separate, time-consuming laboratory analysis and avoiding expensive, unreliable, and labor-intensive analyzers.

Suitable commercially available BS&W or water cut (WC) analyzers can be purchased from Phase Dynamics of Richardson, Texas, or Roxar™, an Emerson brand. For example, inline, field-mounted Roxar™ Watercut meters apply sensitive, microwave—resonance technology in order to accurately measure the permittivity of oil/water mixtures in real-time. Full-bore meters can improve wellhead efficiencies and separation processes, and can be easily adjusted for salinity and changing dry-oil densities. Suitable commercially available TDS analyzers can be purchased from Hach of Loveland, Colorado, Emerson, or Yokogawa Electric Corporation. For example, Hach's Intellical® probes accurately measure the following parameters: pH, Dissolved Oxygen (DO), Conductivity (EC), Total Dissolved Solids (TDS), Ammonia, Ammonium, Fluoride, Nitrate, Sodium, and Redox (ORP).

Experiments

Lab tests were conducted to measure the TDS of water exiting a water outlet of a desalter unit separating crude oil, and separately the TDS of remnant water within dry crude oil. The tests proved that salt content in the water outlet stream from a desalter has nearly the same salt content of the remnant water within dry crude oil with a small difference of less than about 4%. Mixing efficiency in systems and processes can be improved further by using commercially available mixers such as PROMiXX® and ProSalt™ (ProSep) mixers. Mixing efficiency refers to mixing efficiency of the injected wash water with the crude in the mixing valve and in the dehydrator or desalter. Table 1 shows certain values comparing the measured TDS results within dry crude oil exiting a desalter and within a water stream exiting a desalter.

TABLE 1

TDS values for dry crude oil exiting a desalter, and water exiting a desalter and a dehydrator.

| Time | 7:00 | 10:00 | 13:00 |
| --- | --- | --- | --- |
| TDS of separated water from crude samples taken at the crude outlet of a second stage desalter (mg/liter) | 7690 | 7530 | 7825 |
| TDS of a water outlet line from second stage desalter (at suction or discharge of desalter recycle pump) (mg/liter) | 7573 | 7444 | 7558 |
| Percent difference between the TDS of the remnant water in dry crude oil and water outlet streams from the second stage desalter (%) | 1.5 | 1.1 | 3.4 |
| TDS of water outlet from first stage desalter (at suction or discharge of desalter recycle pump) (mg/liter) | 8560 | 8876 | 8433 |
| TDS of water outlet from dehydrator (water to WOSEP) (mg/liter) | 22425 | 23320 | 23530 |

In embodiments disclosed here, innovative process control strategies are disclosed also utilizing the measurable transformer currents (amperes) to one or more desalter or dehydrator with insulated electrostatic electrodes to control the interface level and overcome the consequences of frequent interface level malfunction and failures. In one embodiment, current to one or more transformer is slowly increased with an increase of emulsion layer formation, for example in a dehydrator or desalter, and with an increase in the volume percentage of water in the emulsion layer. A greater water content in volume percent results in a greater current. In separation vessels with insulated electrostatic electrodes, voltage can reach 0 and current a maximum, beyond the inversion point of a water-in-oil emulsion at 65 to 75% water cut. This can cause short circuiting.

The transformer current controller in a range from 0 to 50% of a set, maximum current value is utilized to recycle the emulsion layer formed in a crude oil separation vessel to a crude charge pump suction where it will mix with fresh chemical demulsifier and be heated again for breaking the emulsion. In a transformer current range from 50% to 100% of a set, maximum current value, the current controller will override one or more water level controller at the water line from desalters or dehydrators to a WOSEP to immediately dispose of water and/or the emulsion layer before it contacts the electric grid and causes voltage to drop to zero (short-circuiting), and consequently the off-spec crude in terms of salt and BS&W. In other embodiments, current ranges can vary, for example with a current controller overriding water level control at about 40%, 60%, 70% or 80% of a maximum current value to immediately drain water and/or oil-water emulsion from a crude oil separation vessel, rather than recycling emulsion. In certain embodiments, for example, a level indicator (LI) can be physically installed on a vessel and measures the level inside the vessel (a process variable) and then the LI communicates the value to a level controller for calculating the error from a setpoint. The level controller provides an action to adjust the level control valve LCV (manipulated variable) if necessary from 0 to 100% to maintain the level within the setpoint. The setpoint is normally provided manually by operation based on experience, but in embodiments of the present disclosure, the process controller automatically calculates an optimum setpoint for the level controllers.

Parameters in an oil refinery or GOSP that can cause off-spec crude include: (1) low wash water injection rates (wash water rates should generally be maintained at between about 3 to 9 volume percent of a crude oil feed); (2) low demulsifier injection rates (typical injection rates range from between about 1 to 120 ppm of a crude oil feed); (3) low temperature (typical crude temperatures to desalter inlets are between about 110 to 200 F°); (4) malfunction of the electric grids and transformers (in present embodiments, voltage and electric current will be used to monitor the electric grid); (5) poor mixing of the wash water and demulsifier with the crude (differential pressure across mixing valves can be used to change the mixing strength and efficiency); (6) high crude flow rates and lower residence times inside dehydrators and desalters (crude flow rate can be monitored and controlled); (7) injection of incompatible chemicals during oil well workovers and well flowback; (8) high inlet salt content in the crude oil; and (9) high water cut in the crude oil, for example greater than about 30% water by volume.

Any one of or any combination of the above challenges in crude oil processing can lead to high emulsion interface levels in desalters, which leads to voltage drops or increase in electric current and consequently short circuiting. Low voltage or high electric current in the desalters and dehydrators other than the design specification values can cause damage. Typical values are set by commercial desalter vendors. The rag layer (emulsion layer) in units such as desalters can be detected by interface level measurements like the interface level controllers of Agar Corporation or the Levelflex FMP55 guided wave radar. Capacitance technologies or nuclear type measurements can also be used to measure rag layer levels, but these measurements are unreliable and/or expensive. The interface level measurement can be enhanced using fully insulated electrostatic electrodes inside a 6" pipe spool. In embodiments disclosed here, the proposed pipe spool can simultaneously measure the level and destruct or break the emulsion.

The above challenges in GOSP's and refineries can also cause high water cut measured in BS&W and high TDS of separated water, which generally should be below 12,000 ppm. These issues can all affect the final salt-in-crude content of dry processed crude oil and cause off-spec crude for PTB.

In one embodiment, a closed loop controller is programmed and set in a DCS, where set process variables, for example in a GOSP or refinery, include salt content in PTB less than about 10 PTB and BS&W of less than about 0.2 or 0.3 volume percent in a dried, desalted crude oil product. In the closed loop controller, manipulated variables can include any one of or any combination of chemical demulsifier injection rate in ppm of a crude oil inlet, wash water rate as volume percent of a crude oil inlet, desalter current and voltage, mixing valve pressure drop, separation vessel interface level (for a desalter or dehydrator), separation vessel water level, trim heater temperature, stabilizer reboiler temperature, and stripping gas application rate (if stripping gas is available or required for $H_2S$). Prediction models can be developed using artificial intelligence and historical data of a GOSP or refinery. Model predictive controllers (MPC's) and multivariable controllers (MVC's) can be used to control dried, desalted crude oil product specifications below the set process variables of salt content in PTB less than about 10 PTB and BS&W of less than about 0.2 or 0.3 volume percent.

In some embodiments, inline electrostatic emulsion breakers, such as a 6" diameter spool of pipe fitted with insulated electrostatic electrodes, for example, can be utilized to break a water-in-oil or oil-in-water emulsion before recycling it back to a crude charge pump's suction inlet. One or more of such an emulsion breaker prevents accumulation of emulsion in a desalter as a result of emulsion recirculation during long, continuous processing periods. The electric current and voltage supplied to the emulsion breaker can also be utilized to control the flow of the recycled emulsion.

Normally, transformer current in a GOSP or refinery will increase by 30% before the voltage drops and short-circuiting occurs due to rising emulsion levels. One objective of the embodiments disclosed is to utilize the current variation to open a water outlet or drain ahead of the short-circuit. Electric current drawn for a desalter and/or inline emulsion breaker will be utilized as an indication or measure of the volume percentage of water content inside the emulsion stream and will be utilized to control one or more emulsion recirculation valves. Current and/or voltage measure from one or more desalter transformers can be utilized to override the emulsion control from the inline emulsion breaker, or vice versa.

Fully insulated electrostatic electrodes inside a 6" diameter pipe spool, for example, can be installed such that the inlet for an emulsion flow is at the center of the spool and the outlet is at the bottom of the spool (vertically lower) to avoid water accumulation inside the spool.

An oil-in-water or water-in-oil emulsion can be withdrawn from one or more desalters and/or dehydrators at a controlled rate, for example ranging from about 1 gpm, when there is little to no emulsion layer accumulated, and up to about 30 gpm to maintain the interface level using a control valve in combination with reliable interface measurements. Emulsion layer withdrawal rate will also depend upon the vessel size and amount of crude oil to be processed.

Feeding an emulsion layer stream into fully insulated electrodes inside a spool of pipe helps to break the emulsion. When the electrodes are 100% off, this means about 100% water cut is detected. Therefore, the inline emulsion breaker can also be used as indicator to troubleshoot and enhance the desalting process in combination with the salt-in-crude controller and the interface level. Drawn current can be used to measure the volume percentage of water in the emulsion. For example, greater current draw will indicate greater amount of emulsion, and low current draw will indicate a lesser amount of emulsion.

After proceeding through a separate inline emulsion breaker, a crude oil stream can be recycled back to one or more dehydrator and/or desalter inlet to ensure the full re-integration of the broken emulsion layer into the GOSP or refinery process, and to provide the heating from a trim heater to ensure the emulsion is broken. In some embodiments, one or more BS&W controller, optionally in combination with a current controller on the inline emulsion breaker, is used to manipulate the flow of the withdrawn emulsion from between about 1 to 30 gpm. The electric current supplied to the inline emulsion breaker can be utilized to control and override the BS&W analyzer to increase or decrease the flow of the recycled emulsion. Mixing efficiency between wash water and crude oil is important to embodiments of the present disclosure, and conventional mixing valves can provide more than 95% mixing efficiency, based on lab results. Mixing efficiency can be improved further by using the commercially available PROMiXX® and ProSalt™ (ProSep) mixers, for example vortex mixers.

Referring first to FIG. 1, a schematic diagram is shown for an integrated GOSP of the present disclosure with real-time process control for controlling salt-in-crude content and water content of produced dry crude oil. TDS and BS&W real-time, online measurements can be used to calculate and monitor real-time salt-in-crude content in PTB for dried, desalted, processed crude oil. Desalter transformer electric current control (measured amps) allows for emulsion interface level control. In GOSP system and process 100, inlet wet crude oil at stream 102 enters and is mixed with one or more, optional, chemical demulsifiers provided via demulsifier stream 104, control valve 106, and demulsifier stream 108. Mixed wet crude oil and optional chemical demulsifier proceeds via stream 110 to be mixed with wash water (fresh in addition to or alternative to recycle) from wash water inlet stream 116, control valve 118, and wash water inlet stream 120. At stream 110, in the embodiment shown for example, water cut (volume percent water of the mixed feed) is measured via water cut meter 112 and total dissolved solids is measured via TDS meter 114. Inlet wet crude may be treated in units preceding system 100 such as one or more HPPT, LPPT, and/or LPDT (not pictured).

Mixed wet crude oil, optional demulsifier, and wash water in stream 122 is next mixed with emulsion recycle from stream 124 and control valve 178 and proceeds to crude charge pump 126 to be pumped via stream 128 to trim heater 130 for heating. A temperature indicating control (TIC) 136 measures, monitors, and controls the desired temperature of stream 140 via signal 138 to control valve 134, which itself controls inlet heating stream 132 to trim heater 130, and cooled fluid proceeds out of trim heater 130 via stream 142. Trim heater 130 can include any one of or any combination of indirect heat exchangers known in the art, such as shell and tube heat exchangers. Heated mixed oil, optional demulsifier, and wash water in stream 140 is optionally further mixed with recycle water from stream 144 and control valve 146, and proceeds via stream 150 to mixing valve 152. A differential pressure indicator and control 156 at stream 158 controls mixing valve 152 via signal 154 to ensure efficient mixing of the components in stream 150, for example approaching 100% mixing efficiency. Other pressure indicators and temperature indicators can exist, not pictured, for example preceding mixing valve 152. Mixed stream 158 proceeds into desalter 160 (which in other embodiments could include a separate or integrated dehydrator). Desalter 160 includes an emulsion interface 162, optionally comprising a weir, an electric grid comprising fully insulated electrostatic electrodes 164, and one or more transformer 166 including a current meter 168 and a voltage meter 170.

As shown in FIG. 1, water separating to the bottom of desalter 160 exits via stream 163, and TDS meter 196 measures in real-time TDS in the water, providing the data via signal 190 to PTB controller 188. Dried, desalted crude oil for export, or further stabilization treatment, if necessary, exits desalter 160 via stream 182 where BS&W (water cut) meter 184 measures in real-time the BS&W content of stream 182, mostly to determine the water content of the dried, desalted crude oil. BS&W meter 184 sends the measurements in real-time via signal 186 to PTB controller 188. PTB controller 188, using online, real-time readings from TDS meter 196 and BS&W meter 184 calculates in real-time, monitors, and controls in real-time the PTB salt and/or water content in stream 182 such that the dried, desalted crude oil meets set specifications, such as for example less than about 10 PTB salt and less than about 0.2 or 0.3 volume percent water. PTB controller 188 applies, for example, Equation 1 to calculate the PTB salt from BS&W and TDS measurements. To meet said specifications, process variables can be changed, such as increased or decreased chemical demulsifier, wash water content, trim heating, differential pressure across valves for mixing, and/or emulsion recycle.

Current meter 168 and a voltage meter 170 of desalter 160 provide signal 172 to current controller 174 for control of valve 178 via signal 176. When current supplied to one or more transformer 166 is between 0% and about 40%, 50%, 60%, 70%, or 80% of an acceptable, set maximum current value (for example set by the desalter vendor), the current controller 174 opens control valve 178 in an increasing amount corresponding to increasing current to remove the emulsion (rag) layer in desalter 160 via stream 180 proximate emulsion interface 162 for recycle via stream 124. When current supplied to one or more transformer 166 is between about 50% and 100% of an acceptable, set maximum current value (for example set by the desalter vendor), the current controller 174 signals via signal 177 flow controller 189 to open drain valve 193 by signal 191. Level controller 192 also provides data to flow controller 189 via signal 194 regarding the level of water and/or emulsion in desalter 160. In normal operation between 0% and 50% of an acceptable, set maximum current value, water exiting desalter 160 at stream 163 can be recycled to stream 140 via stream 163, pump 197, stream 198, stream 148, control valve 146, and stream 144. Between about 40%, 50%, 60%, 70%, or 80% and 100% of an acceptable, set maximum current value and/or at a higher than acceptable water and/or emulsion level based on level controller 192, flow controller 189 opens drain valve 193 via signal 191 to allow excess water and/or emulsion to flow out of the system via lines 199 and 195, for example to a WOSEP (not pictured).

To stabilize level controller 192 and pump 197 operation, a flow controller 189 is provided to maintain certain stable flow. The level controller 192 is cascaded to the flow controller 189. In some embodiments, the flow controller 189 setpoint is provided by the level controller 192. Flow controller 189 is considered slave while the level controller 192 is the master controller. In a cascade control arrangement, there are two (or more) controllers of which one controller's output drives the set point of another controller. For example: a level controller driving the set point of a flow controller to keep the level at its set point.

Emulsion and water level set value or normal level in desalter 160 will be set during the design and operation of the desalter 160. For example water and/or emulsion level control will be maintained between a minimum limit of about 15% to maximum level of about 45% in desalter 160.

Level controller 192 in some embodiments can measure either or both the water level and the emulsion level. Flow controller 189 can maintain a fixed flow rate and fixed valve opening at drain valve 193. For example, when the emulsion level increases to a certain point that will touch the electric grid 164 and cause a short circuit, level controller 192 will provide a new setpoint to the flow controller 189 to further open the drain valve 193 and allow more water flow to exit via stream 195. Flow controller 189 will maintain this new high flow rate, until indicated otherwise by level controller 192. When the emulsion level starts to drop in desalter 160 to a certain limit and to prevent oil from exiting with the water, the level controller 192 will send a new setpoint to the flow controller 189 to partially or fully close the valve 193 and decrease the flow. The new flow will be maintained until a new set point from the level controller 192 is received by flow controller 189.

The current controller 174 controls transformer current based on measurements from current meter 168. Normally the current is low which indicates that the electric grid is immersed inside the oil phase of desalter 160, which is less conductive than water, to separate entrained water droplets in the oil via electrostatic coalescence. Low current is desirable. When the current measurements start to increase, this is considered as indication of encroachment of water level and/or emulsion to the electric grid 164, as the emulsion and water conductivity is much higher than the oil. When the current controller 174 reaches a certain setpoint (higher than normal current), the controller will act and send a signal (setpoint) to the flow controller 189 to open the drain valve 193 to let more water out via stream 195 and reduce the level inside the desalter 160 and consequently prevent the water or emulsion from touching the electric grid, which advantageously, surprisingly and unexpectedly avoids short-circuiting or tripping which occurs in the prior art.

Figure 2:
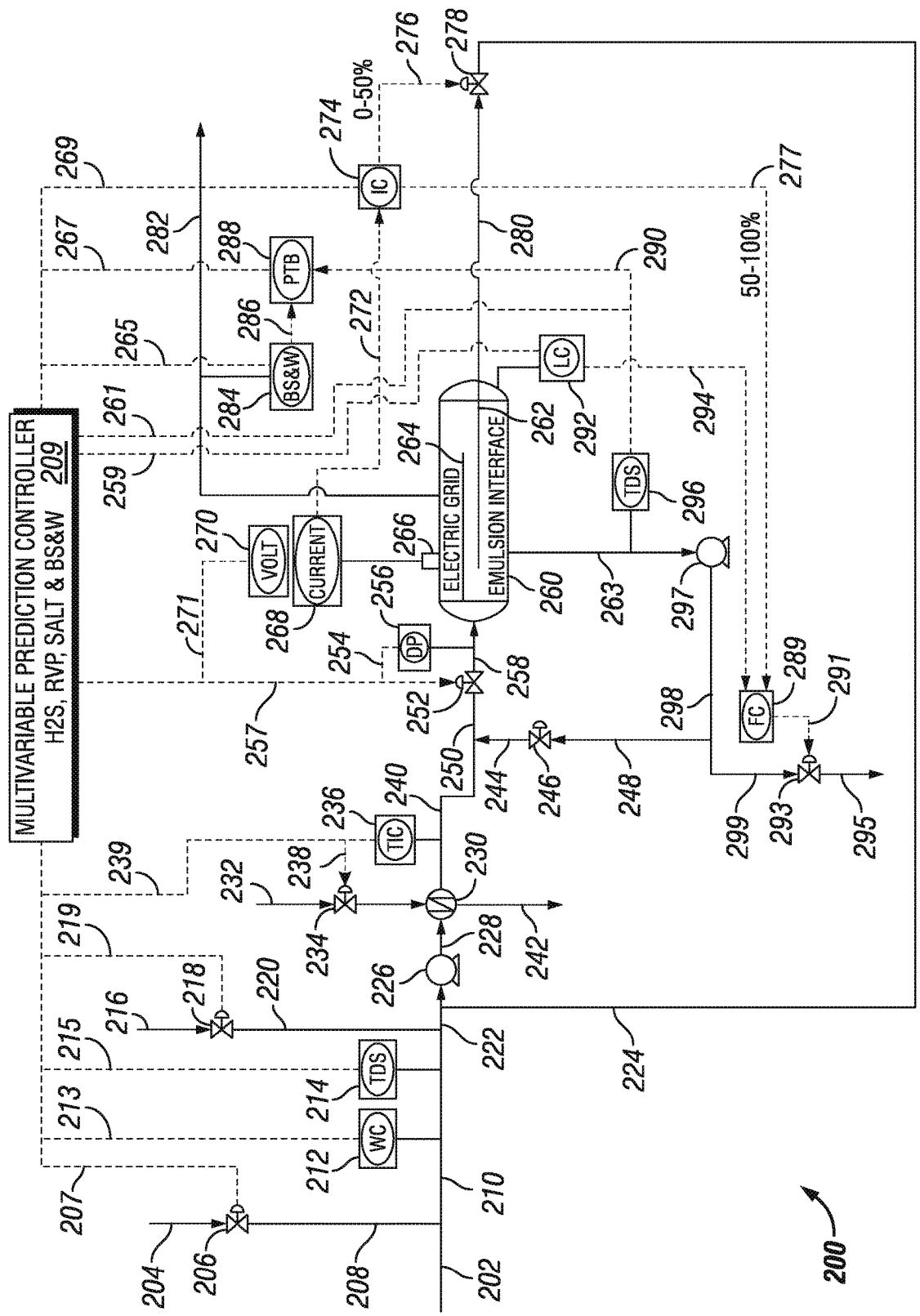
FIG. 2 is a schematic diagram showing an integrated GOSP of the present disclosure with real-time process control using a multivariable prediction controller (MPC) for controlling salt-in-crude content and water content of produced dry crude oil along with $H_2S$, RVP, and BS&W content.

FIG. 2 is a schematic diagram showing an integrated GOSP of the present disclosure with real-time process control using a multivariable prediction controller (MPC) for controlling salt-in-crude content of produced dry crude oil along with H$_2$S, RVP, and BS&W content. Desalter transformer electric current control (measured amps) allows for emulsion interface level control. In GOSP system and process 200, inlet wet crude oil at stream 202 enters and is mixed with one or more, optional, chemical demulsifiers provided via demulsifier stream 204, control valve 206, and demulsifier stream 208. Multivariable prediction controller (MPC) 209 controls valve 206 via signal 207 to increase or decrease the amount of demulsifier as needed, for example to reach the set variables of GOSP system and process 200, such as a maximum PTB salt and maximum volume percent of water in dried, desalted crude oil at the system and process outlet. Mixed wet crude oil and optional chemical demulsifier proceeds via stream 210 to be mixed with wash water (fresh in addition to or alternative to recycle) from wash water inlet stream 216, control valve 218, and wash water inlet stream 220. At stream 210, in the embodiment shown for example, water cut (volume percent water of the mixed feed) is measured via water cut meter 212 and total dissolved solids is measured via TDS meter 214. Signal 213 provides data from water cut meter 212 to MPC 209, and signal 215 provides data from TDS meter 214 to MPC 209. Signal 219 from MPC 209 can control the amount of wash water added to the inlet oil feed via control of valve 218. For example, for higher salinity oils from a hydrocarbon bearing reservoir, identified at TDS meter 214, additional wash water can be signaled to be added at control valve 218 via signal 219 from MPC 209. Signals described throughout can be wired or wireless electronic signals proceeding one-way or two ways.

Mixed wet crude oil, optional demulsifier, and wash water in stream 222 is next mixed with emulsion recycle from stream 224 and control valve 278 and proceeds to crude charge pump 226 to be pumped via stream 228 to trim heater 230 for heating. A temperature indicating control (TIC) 236 measures, monitors, and controls the desired temperature of stream 240 via signals 238 and 239 to control valve 234 and MPC 209, respectively. Control valve 234 itself controls inlet heating stream 232 to trim heater 230, and cooled fluid proceeds out of trim heater 230 via stream 242. Trim heater 230 can include any one of or any combination of indirect heat exchangers known in the art, such as shell and tube heat exchangers. Heated mixed oil, optional demulsifier, and wash water in stream 240 is optionally further mixed with recycle water from stream 244 and control valve 246, and proceeds via stream 250 to mixing valve 252. A differential pressure indicator and control 256 at stream 258 controls mixing valve 252 via signals 254 and 257 to ensure efficient mixing of the components in stream 250, for example about 90% or about 100% mixing efficiency. For example, if off-spec crude is detected in stream 282, MPC 209 can increase or decrease any one of or any combination of demulsifier injection, wash water injection, trim heating, or mixing at mixing valve 252 via control of the differential pressure across the valve.

Mixed stream 258 proceeds into desalter 260 (which in other embodiments could include a separate or integrated dehydrator). Desalter 260 includes an emulsion interface 262, optionally comprising a weir, an electric grid comprising fully insulated electrostatic electrodes 264, and one or more transformer 266 including a current meter 268 and a voltage meter 270. Current meter 268 and voltage meter 270 provide real-time current and voltage data, respectively, to MPC 209 via signal 271.

As shown in FIG. 2, water separating to the bottom of desalter 260 exits via stream 263, and TDS meter 296 measures in real-time TDS in the water, providing the data via signal 290 to PTB controller 288. Dried, desalted crude oil for export exits desalter 260 via stream 282 where BS&W meter 284 measures in real-time the BS&W content of stream 282, mostly to determine the water content of the dried, desalted crude oil. BS&W meter 284 sends the measurements in real-time via signal 286 to PTB controller 288. PTB controller 288, using online, real-time readings from TDS meter 296 and BS&W meter 284 calculates in real-time, monitors, and controls in real-time the PTB salt and/or water content in stream 282, in addition to or alternative to MPC 209, such that the dried, desalted crude oil meets set specifications, such as for example less than about 10 PTB salt and less than about 0.2 volume percent water. PTB controller 288 applies, for example, Equation 1 to calculate the PTB from BS&W and TDS measurements. TDS meter 296, BS&W meter 284, and PTB controller 288 in the embodiment shown are in wired in addition to or alternative to wireless communication with MPC 209 via signals 261, 265, and 267, respectively.

Current meter 268 and voltage meter 270 of desalter 260 provide signal 272 to current controller 274 for control of valve 278 via signal 276. When current supplied to one or more transformer 266 is between about 0% and 50% of an acceptable, set maximum current value (for example set by the desalter vendor), the current controller 274, in addition to or alternative to MPC 209, opens valve 278 in an increasing amount corresponding to increasing current to remove the emulsion (rag) layer in desalter 260 via stream 280 for recycle via stream 224. When current supplied to one or more transformer 266 is between 50% and 100% of an acceptable, set maximum current value (for example set by the desalter vendor), the current controller 274, in addition to or alternative to MPC 209, signals via signal 277 flow controller 289 to open drain valve 293 by signal 291. In the embodiment shown, current controller 274 is in wired in addition to or alternative to wireless communication with MPC 209 via signal 269.

Level controller 292 also provides data to flow controller 289 via signal 294 regarding the level of water and/or emulsion in desalter 260. In normal operation between 0% and 50% of an acceptable, set maximum current value, water exiting desalter 260 at stream 263 can be recycled to stream 240 via stream 263, pump 297, stream 298, stream 248, control valve 246, and stream 244. Between 50% and 100% of an acceptable, set maximum current value and/or at a higher than acceptable emulsion level and/or water level based on level controller 292, flow controller 289 opens drain valve 293 via signal 291 to allow excess water and/or emulsion to flow out of the system via lines 299 and 295, for example to a WOSEP. In the embodiment shown, level controller 292 is in wired in addition to or alternative to wireless communication with MPC 209 via signal 259. Either or both level controller 292 and/or current controller 274 can signal flow controller 289 to a new set point for control of valve 293, where flow controller 289 is slave to level controller 292 and current controller 274, which avoids short circuiting of electric grid 264 in desalter 260 when a water/emulsion level in desalter 260 rises.

Figure 3:
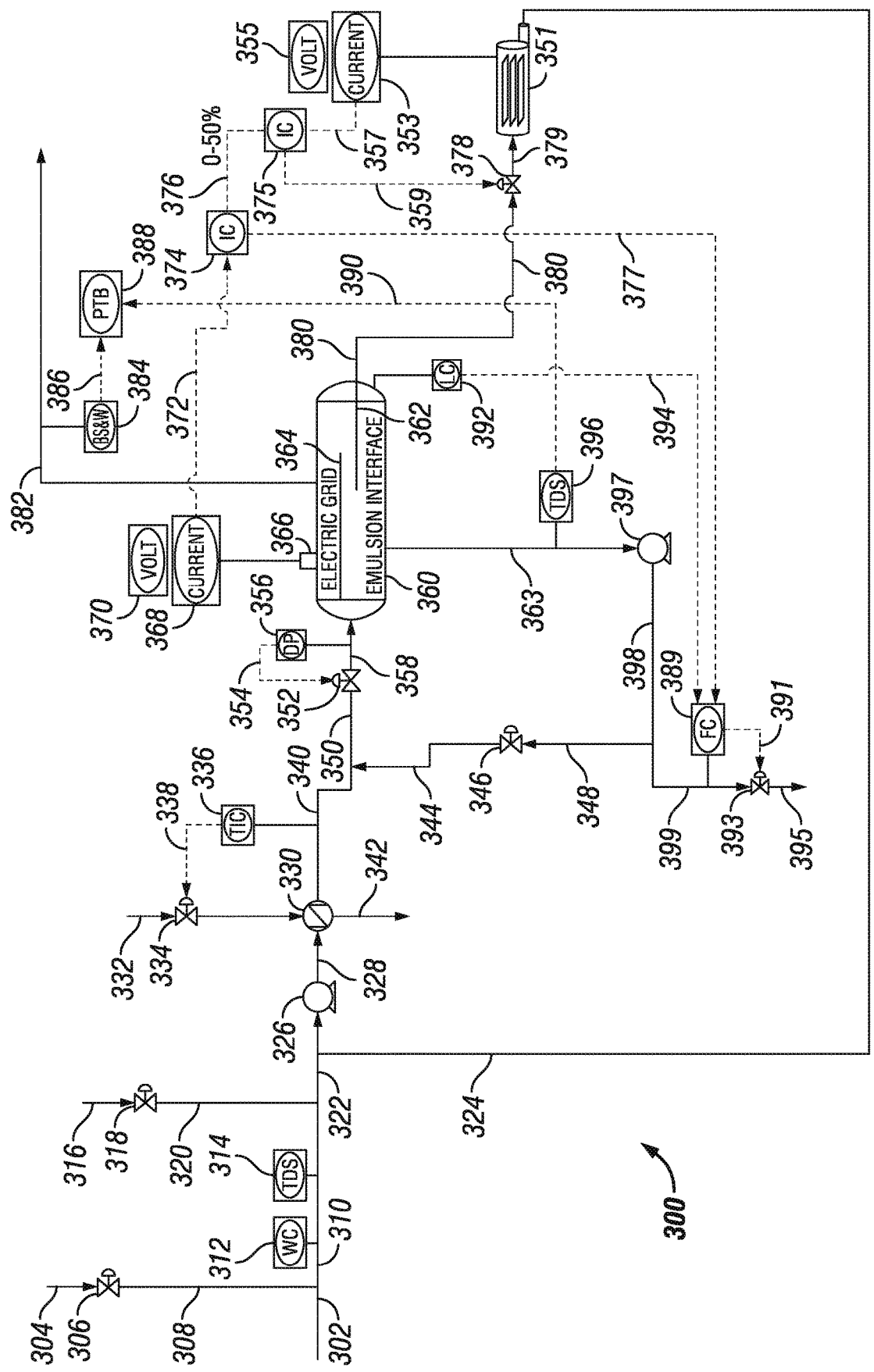
FIG. 3 is a schematic diagram showing an integrated GOSP of the present disclosure with real-time process control for controlling salt-in-crude content and water content of produced dry crude oil, including an inline electrostatic emulsion breaker.

FIG. 3 is a schematic diagram showing an integrated GOSP of the present disclosure with real-time process control for controlling salt-in-crude content of produced dry crude oil, including an inline electrostatic emulsion breaker. TDS and BS&W real-time, online measurements can be used to calculate and monitor real-time salt-in-crude content in PTB for dried, desalted processed crude oil. Desalter transformer electric current control (measured amps) allows for emulsion interface level control. In GOSP system and process 300, inlet wet crude oil at stream 302 enters and is mixed with one or more, optional, chemical demulsifiers provided via demulsifier stream 304, control valve 306, and demulsifier stream 308. Mixed wet crude oil and optional chemical demulsifier proceeds via stream 310 to be mixed with wash water (fresh in addition to or alternative to recycle) from wash water inlet stream 316, control valve 318, and wash water inlet stream 320. At stream 310, in the embodiment shown for example, water cut (volume percent water of the mixed feed) is measured via water cut meter 312 and total dissolved solids is measured via TDS meter 314.

Mixed wet crude oil, optional demulsifier, and wash water in stream 322 is next mixed with emulsion recycle from stream 324 and control valve 378 and proceeds to crude charge pump 326 to be pumped via stream 328 to trim heater 330 for heating. A temperature indicating control (TIC) 336 measures, monitors, and controls the desired temperature of stream 340 via signal 338 to control valve 334, which itself controls inlet heating stream 332 to trim heater 330, and cooled fluid proceeds out of trim heater 330 via stream 342. Trim heater 330 can include any one of or any combination of indirect heat exchangers known in the art, such as shell and tube heat exchangers. Heated mixed oil, optional demulsifier, and wash water in stream 340 is optionally further mixed with recycle water from stream 344 and control valve 346, and proceeds via stream 350 to mixing valve 352. A differential pressure indicator and control 356 at stream 358 controls mixing valve 352 via signal 354 to ensure efficient mixing of the components in stream 350. Mixed stream 358 proceeds into desalter 360 (which in other embodiments could include a separate dehydrator). Desalter 360 includes an emulsion interface 362, optionally comprising a weir, an electric grid comprising fully insulated electrostatic electrodes 364, and one or more transformer 366 including a current meter 368 and a voltage meter 370.

As shown in FIG. 3, water separating to the bottom of desalter 360 exits via stream 363, and TDS meter 396 measures in real-time TDS in the water, providing the data via signal 390 to PTB controller 388. Dried, desalted crude oil for export exits desalter 360 via stream 382 where BS&W meter 384 measures in real-time the BS&W content of stream 382, mostly to determine the water content of the dried, desalted crude oil. BS&W meter 384 sends the measurements in real-time via signal 386 to PTB controller 388. PTB controller 388, using online, real-time readings from TDS meter 396 and BS&W meter 384 calculates in real-time, monitors, and controls in real-time the PTB and/or water content in stream 382 such that the dried, desalted crude oil meets set specifications, such as for example less than about 10 PTB salt and less than about 0.2 volume percent water. PTB controller 388 applies, for example, Equation 1 to calculate the PTB from BS&W and TDS measurements. To meet said specifications, process variables can be changed, such as increased or decreased chemical demulsifier injection, wash water content, trim heating, and/or emulsion recycle.

Current meter 368 and a voltage meter 370 of desalter 360 provide signals 372 and 376 to current controllers 374 and 375, respectively, for control of valve 378 via signal 359. When current supplied to one or more transformer 366 is between about 0% and 50% of an acceptable, set maximum current value (for example set by the desalter vendor), the current controllers 374 and 375 open valve 378 in an increasing amount corresponding to increasing current to remove the emulsion (rag) layer in desalter 360 via stream 380 for recycle via stream 324. In the embodiment of FIG. 3, the emulsion in stream 380 proceeds under normal operation between 0% and 50% of an acceptable, set maximum current value through valve 378 and stream 379 to inline emulsion breaker with insulated electrostatic electrodes 351. Current meter 353 and voltage meter 355 of inline emulsion breaker with insulated electrostatic electrodes 351 provide via signal 357 data to current controller 375 regarding voltage and current supplied to inline emulsion breaker with insulated electrostatic electrodes 351. Inline emulsion breaker with insulated electrostatic electrodes 351, for example a 6" spool of pipe with insulated electrostatic electrodes, optionally placed horizontally or vertically, helps break emulsions such as tight emulsions.

When current supplied to one or more transformer 366 and/or inline emulsion breaker with insulated electrostatic electrodes 351 is between 50% and 100% of an acceptable, set maximum current value (for example set by the desalter vendor or user), the current controllers 374 and/or 375 signal via signal 377 flow controller 389 to open drain valve 393 by signal 391. Control valve 378 can be opened, partially-opened, or closed by signal 359 when drain valve 393 is opened. Level controller 392 also provides data to flow controller 389 via signal 394 regarding the level of water and/or emulsion in desalter 360. In normal operation between 0% and 50% of an acceptable, set maximum current value, water exiting desalter 360 at stream 363 can be recycled to stream 340 via stream 363, pump 397, stream 398, stream 348, control valve 346, and stream 344. Control valve 346 can be opened, partially-opened, or closed when drain valve 393 is opened. Between 50% and 100% of an acceptable, set maximum current value (for either or both desalter 360 and/or to inline emulsion breaker with insulated electrostatic electrodes 351) and/or at a higher than acceptable emulsion level and/or water level based on level controller 392, flow controller 389 opens drain valve 393 via signal 391 to allow excess water and/or emulsion to flow out of the system via lines 399 and 395, for example to a WOSEP.

Figure 4:
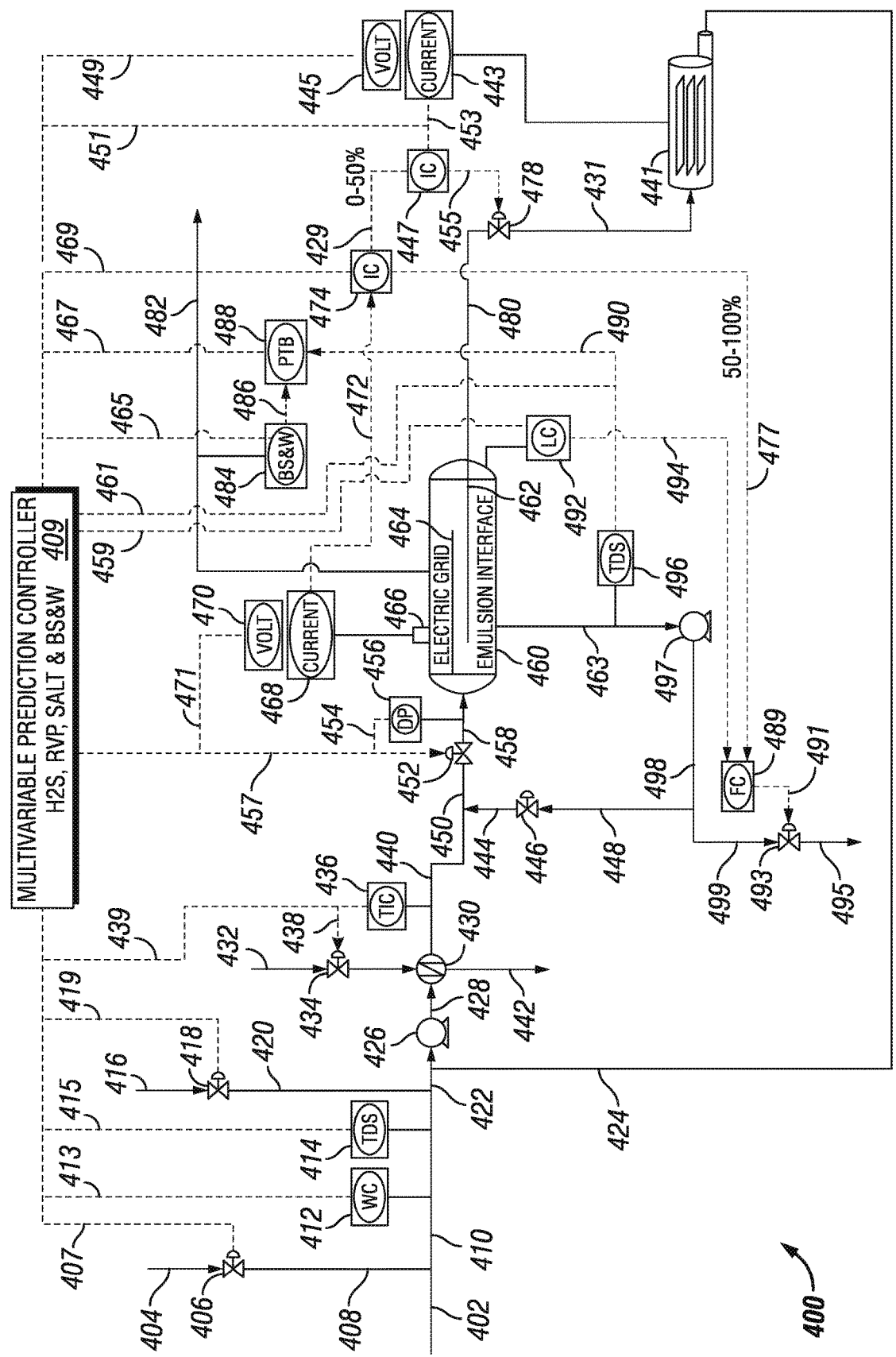
FIG. 4 is a schematic diagram showing an integrated GOSP of the present disclosure with real-time process control using an MPC for controlling salt-in-crude content and water content of produced dry crude oil along with $H_2S$, RVP, and BS&W content, including an inline electrostatic emulsion breaker.

FIG. 4 is a schematic diagram showing an integrated GOSP of the present disclosure with real-time process control using an MPC for controlling salt-in-crude content of produced dry crude oil along with $H_2S$, RVP, and BS&W content, including an inline electrostatic emulsion breaker. Desalter transformer electric current control (measured amps) allows for emulsion interface level control. In GOSP system and process 400, inlet wet crude oil at stream 402 enters and is mixed with one or more, optional, chemical demulsifiers provided via demulsifier stream 404, control valve 406, and demulsifier stream 408. Multivariable prediction controller (MPC) 409 controls valve 406 via signal 407 to increase or decrease the amount of demulsifier as needed, for example to reach the set variables of GOSP system and process 400, such as a maximum PTB salt and maximum volume percent of water in dried, desalted crude oil at the system and process outlet.

Mixed wet crude oil and optional chemical demulsifier proceeds via stream 410 to be mixed with wash water (fresh in addition to or alternative to recycle) from wash water inlet stream 416, control valve 418, and wash water inlet stream 420. At stream 410, in the embodiment shown for example, water cut (volume percent water of the mixed feed) is measured via water cut meter 412 and total dissolved solids is measured via TDS meter 414. Signal 413 provides data from water cut meter 412 to MPC 409, and signal 415 provides data from TDS meter 414 to MPC 409. Signal 419 from MPC 409 can control the amount of wash water added to the inlet oil feed via control of valve 418. For example, for higher salinity oils from a hydrocarbon bearing reservoir, identified at TDS meter 414, additional wash water can be signaled to be added at control valve 418 via signal 419 from MPC 409. Signals of the present disclosure can be transmitted both through wired and wireless communications. Signals can be one-way or two-ways between meters, controllers, and MPC's.

Mixed wet crude oil, optional demulsifier, and wash water in stream 422 is next mixed with optional emulsion recycle from stream 424 and control valve 478 and proceeds to crude charge pump 426 to be pumped via stream 428 to trim heater 430 for heating. A temperature indicating control (TIC) 436 measures, monitors, and controls the desired temperature of stream 440 via signals 438 and 439, along with or alternative to MPC 409, to control valve 434, which itself controls inlet heating stream 432 to trim heater 430, and cooled fluid proceeds out of trim heater 430 via stream 442. Trim heater 430 can include any one of or any combination of indirect heat exchangers known in the art, such as shell and tube heat exchangers. Heated mixed oil, optional demulsifier, and wash water in stream 440 is optionally further mixed with recycle water from stream 444 and control valve 446, and proceeds via stream 450 to mixing valve 452. A differential pressure indicator and control 456 at stream 458 controls mixing valve 452 via signals 454 and 457 to ensure efficient mixing of the components in stream 450, for example approaching 100% mixing efficiency. For example, if off-spec crude is detected in stream 482, MPC 409 can increase or decrease any one of or any combination of demulsifier injection, wash water injection, trim heating, or mixing at mixing valve 452.

Mixed stream 458 proceeds into desalter 460 (which in other embodiments could include a separate dehydrator). Desalter 460 includes an emulsion interface 462, optionally comprising a weir, an electric grid comprising fully insulated electrostatic electrodes 464, and one or more transformer 466 including a current meter 468 and a voltage meter 470. Current meter 468 and voltage meter 470 provide real-time current and voltage data, respectively, to MPC 209 via signal 471.

As shown in FIG. 4, water separating to the bottom of desalter 460 exits via stream 463, and TDS meter 496 measures in real-time TDS in the water, providing the data via signal 490 to PTB controller 488. Dried, desalted crude oil for export exits desalter 460 via stream 482 where BS&W meter 484 measures in real-time the BS&W content of stream 482, mostly to determine the water content of the dried, desalted crude oil. BS&W meter 484 sends the measurements in real-time via signal 486 to PTB controller 488. PTB controller 488, using online, real-time readings from TDS meter 496 and BS&W meter 484 calculates in real-time, monitors, and controls in real-time the PTB and/or water content in stream 482, in addition to or alternative to MPC 409, such that the dried, desalted crude oil meets set specifications, such as for example less than about 10 PTB salt and less than about 0.2 volume percent water. PTB controller 488 applies, for example, Equation 1 to calculate the PTB from BS&W and TDS measurements. TDS meter 496, BS&W meter 484, and PTB controller 488 in the embodiment shown are in wired in addition to or alternative to wireless communication with MPC 409 via signals 461, 465, and 467, respectively. Controllers of the present disclosure can also apply historical data of the systems to model via artificial intelligence efficient changes to meet set specifications for crude oil. For example, where a certain type of wet crude is supplied and recognized by the system controllers or meters, variables can be adjusted, such as heating and wash water, to efficiently meet the required specifications for dried, desalted crude oil.

Current meter 468 and a voltage meter 470 of desalter 460 provide signals 472 and 429 to current controllers 474 and 447, respectively, for control of valve 478 via signal 455. When current supplied to one or more transformer 466 is between about 0% and 40%, 50%, 60%, 70%, or 80% of an acceptable, set maximum current value (for example set by the desalter vendor), the current controllers 474 and/or 447, in addition to or alternative to MPC 409, open valve 478 in an increasing amount corresponding to increasing current to remove the emulsion (rag) layer in desalter 460 via stream 480 for recycle via stream 424. Current controllers 474 and 447 are in communication with MPC 409 by signals 469 and 451, respectively.

In the embodiment of FIG. 4, the emulsion in stream 480 proceeds under normal operation between 0% and 50% of an acceptable, set maximum current value through valve 478 and stream 431 to inline emulsion breaker with insulated electrostatic electrodes 441. Current meter 443 and voltage meter 445 of inline emulsion breaker with insulated electrostatic electrodes 441 provide via signal 453 data to current controller 447 regarding voltage and current supplied to inline emulsion breaker with insulated electrostatic electrodes 441. Inline emulsion breaker with insulated electrostatic electrodes 441, for example a 6" spool of pipe with insulated electrostatic electrodes, optionally placed horizontally or vertically, helps break emulsions such as tight emulsions. Current meter 443 and voltage meter 445 of inline emulsion breaker with insulated electrostatic electrodes 441 are also in electrical communication with MPC 409 via wired and/or wireless signals 451, 449, respectively to provide data to and receive data from, as necessary, MPC 409.

When current supplied to one or more transformer 466 and/or inline emulsion breaker with insulated electrostatic electrodes 441 is between 50% and 100% of an acceptable, set maximum current value (for example set by the desalter vendor or user), the current controllers 474 and/or 447 signal via signal 477 flow controller 489 to open drain valve 493 by signal 491. Control valve 478 can be opened, partially-opened, or closed by signal 455 when drain valve 493 is opened. Level controller 492 also provides data to flow controller 489 via signal 494 regarding the level of water and/or emulsion in desalter 460. In normal operation between 0% and 50% of an acceptable, set maximum current value, water exiting desalter 460 at stream 463 can be recycled to stream 440 via stream 463, pump 497, stream 498, stream 448, control valve 446, and stream 444. Control valve 446 can be opened, partially-opened, or closed when drain valve 493 is opened. Between 50% and 100% of an acceptable, set maximum current value (for either or both desalter 460 and/or to inline emulsion breaker with insulated electrostatic electrodes 441) and/or at a higher than acceptable emulsion level and/or water level based on level controller 492, flow controller 489 opens drain valve 493 via signal 491 to allow excess water and/or emulsion to flow out of the system via lines 499 and 495, for example to a WOSEP. For example, a water level/emulsion controller can be cascaded directly to a flow controller and provide its setpoint. If current starts to increase beyond a certain setpoint, which is indication of water encroaching into the electric grids, then the current controller will override the level control and provide a new setpoint to the flow controller to quickly open the valve and reduce the level.

Figure 5:
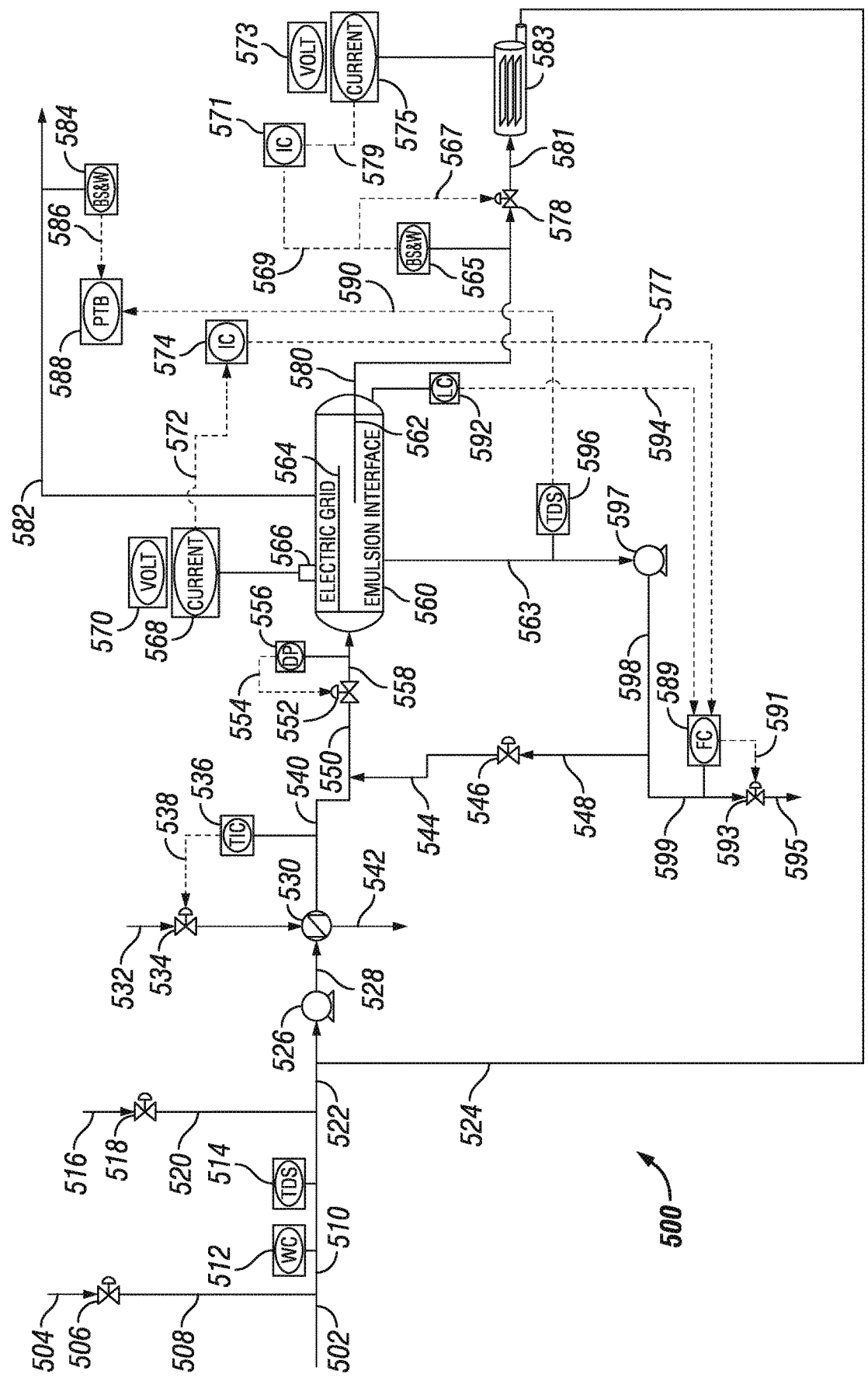
FIG. 5 is a schematic diagram showing an integrated GOSP of the present disclosure with real-time process control for controlling salt-in-crude content and water content of produced dry crude oil, including an inline electrostatic emulsion breaker.

FIG. 5 is a schematic diagram showing an integrated GOSP of the present disclosure with real-time process control for controlling salt-in-crude content of produced dry crude oil, including an inline electrostatic emulsion breaker. TDS and BS&W real-time, online measurements can be used to calculate and monitor real-time salt-in-crude content in PTB for dried, desalted processed crude oil. Desalter transformer electric current control (measured amps) allows for emulsion interface level control. In GOSP system and process 500, inlet wet crude oil at stream 502 enters and is mixed with one or more, optional, chemical demulsifiers provided via demulsifier stream 504, control valve 506, and demulsifier stream 508. Mixed wet crude oil and optional chemical demulsifier proceeds via stream 510 to be mixed with wash water (fresh in addition to or alternative to recycle) from wash water inlet stream 516, control valve 518, and wash water inlet stream 520. At stream 510, in the embodiment shown for example, water cut (volume percent water of the mixed feed) is measured via water cut meter 512 and total dissolved solids is measured via TDS meter 514.

Mixed wet crude oil, optional demulsifier, and wash water in stream 522 is next mixed with emulsion recycle from stream 524 and control valve 578 and proceeds to crude charge pump 526 to be pumped via stream 528 to trim heater 530 for heating. A temperature indicating control (TIC) 536 measures, monitors, and controls the desired temperature of stream 540 via signal 538 to control valve 534, which itself controls inlet heating stream 532 to trim heater 530, and cooled fluid proceeds out of trim heater 530 via stream 542. Trim heater 530 can include any one of or any combination of indirect heat exchangers known in the art, such as shell and tube heat exchangers. Heated mixed oil, optional demulsifier, and wash water in stream 540 is optionally further mixed with recycle water from stream 544 and control valve 546, and proceeds via stream 550 to mixing valve 552. A differential pressure indicator and control 556 at stream 558 controls mixing valve 552 via signal 554 to ensure efficient mixing of the components in stream 550. Not pictured, any stream preceding stream 558 can also have a pressure gauge for pressure indicator and control 556 to gauge differential pressure across mixing valve 552, similar to the embodiments of other figures. Mixed stream 558 proceeds into desalter 560 (which in other embodiments could include a separate or integrated dehydrator). Desalter 560 includes an emulsion interface 562, optionally comprising a weir, an electric grid comprising fully insulated electrostatic electrodes 564, and one or more transformer 566 including a current meter 568 and a voltage meter 570.

As shown in FIG. 5, water separating to the bottom of desalter 560 exits via stream 563, and TDS meter 596 measures in real-time TDS in the water, providing the data via signal 590 to PTB controller 588. Dried, desalted crude oil for export exits desalter 560 via stream 582 where BS&W meter 584 measures in real-time the BS&W content of stream 582, mostly to determine the water content of the dried, desalted crude oil. BS&W meter 584 sends the measurements in real-time via signal 586 to PTB controller 588. PTB controller 588, using online, real-time readings from TDS meter 596 and BS&W meter 584 calculates in real-time, monitors, and controls in real-time the PTB salt and/or water content in stream 582 such that the dried, desalted crude oil meets set specifications, such as for example less than about 10 PTB salt and less than about 0.2 volume percent water. PTB controller 588 applies, for example, Equation 1 to calculate the PTB from BS&W and TDS measurements. To meet said specifications, process variables can be changed, such as increased or decreased chemical demulsifier, wash water content, trim heating, differential pressure across mixing valves, and/or emulsion recycle.

Current meter 568 and a voltage meter 570 of desalter 560 provide signal 572 to current controller 574 for control of flow controller 589 via signal 577. When current supplied to one or more transformer 566 is between 0% and 50% of an acceptable, set maximum current value (for example set by the desalter vendor), the current controller 574 keeps closed drain valve 593 via signal 577 to flow controller 589 and via signal 591 to drain valve 593. In the embodiment of FIG. 5, the emulsion in stream 580 proceeds under normal operation between 0% and 50% of an acceptable, set maximum current value through valve 578 and stream 581 to inline emulsion breaker with insulated electrostatic electrodes 583. Current meter 575 and voltage meter 573 of inline emulsion breaker with insulated electrostatic electrodes 583 provide via signal 579 data to current controller 571 regarding voltage and current supplied to inline emulsion breaker with insulated electrostatic electrodes 583. Inline emulsion breaker with insulated electrostatic electrodes 583, for example a 6" spool of pipe with insulated electrostatic electrodes, optionally placed horizontally or vertically, helps break emulsions such as tight emulsions.

When current supplied to inline emulsion breaker with insulated electrostatic electrodes 583 is between about 50% and 100% of an acceptable, set maximum current value, or other value such as about 40%, 60%, 70%, or 80%, control valve 578 can be closed via signals 579, 569, and 567 to prevent short circuiting of inline emulsion breaker with insulated electrostatic electrodes 583. BS&W analyzer 565 is installed to measure the volume percent of water inside the withdrawn emulsion layer. BS&W analyzer 565 is used to manipulate the flow of the withdrawn emulsion from between about 1 to 30 gpm. Electric current measured at current meter 575 can be utilized to control and override BS&W analyzer 565 to increase or decrease the flow of the recycled emulsion.

BS&W analyzer 565 is used to control withdrawal of the emulsion layer from the desalter 560 to inline emulsion breaker with insulated electrostatic electrodes 583. At near-zero BS&W readings (low current at current controller 571), the control valve 578 will be maintained open to pass 1 gpm of emulsion continuously. When BS&W content begins to increase, the control valve 578 will start to open gradually to withdraw the emulsion layer up to about 30 gpm. The current from the inline emulsion breaker with insulated electrostatic electrodes 583 is used as indication of the water cut and as backup control for the water cut. There is no issue of short circuiting in the inline emulsion breaker with insulated electrostatic electrodes 583, because in some embodiments it comprises coated electrodes that can handle up to 100% water or gas by volume. The BS&W analyzer 565 and current controller 571 can be used as advisory controls to open flow controller 589 to allow more water to flow from the desalter 560 and establish the water level set point.

When current supplied to one or more transformer 566 is between 50% and 100% of an acceptable, set maximum current value (for example set by the desalter vendor or user), the current controller 574 signals via signal 577 flow controller 589 to open drain valve 593 by signal 591. Control valve 578 can be opened, partially-opened, or closed by signal 567 when drain valve 593 is opened, depending on readings from current meter 575 and voltage meter 573 to current controller 571 by signal 579. Level controller 592 also provides data to flow controller 589 via signal 594 regarding the level of water and/or emulsion in desalter 560. In normal operation between 0% and 50% of an acceptable, set maximum current value, water exiting desalter 560 at stream 563 can be recycled to stream 540 via stream 563, pump 597, stream 598, stream 548, control valve 546, and stream 544. Control valve 546 can be opened, partially-opened, or closed when drain valve 593 is opened. Between 50% and 100% of an acceptable, set maximum current value (for either or both desalter 560 and/or to inline emulsion breaker with insulated electrostatic electrodes 583) and/or at a higher than acceptable emulsion level and/or water level based on level controller 592, flow controller 589 opens drain valve 593 via signal 591 to allow excess water and/or emulsion to flow out of the system via lines 599 and 595, for example to a WOSEP. As in other embodiments, current meters and controllers can override level controllers to drain water and/or emulsion from a desalter to prevent short circuiting.

Figure 6:
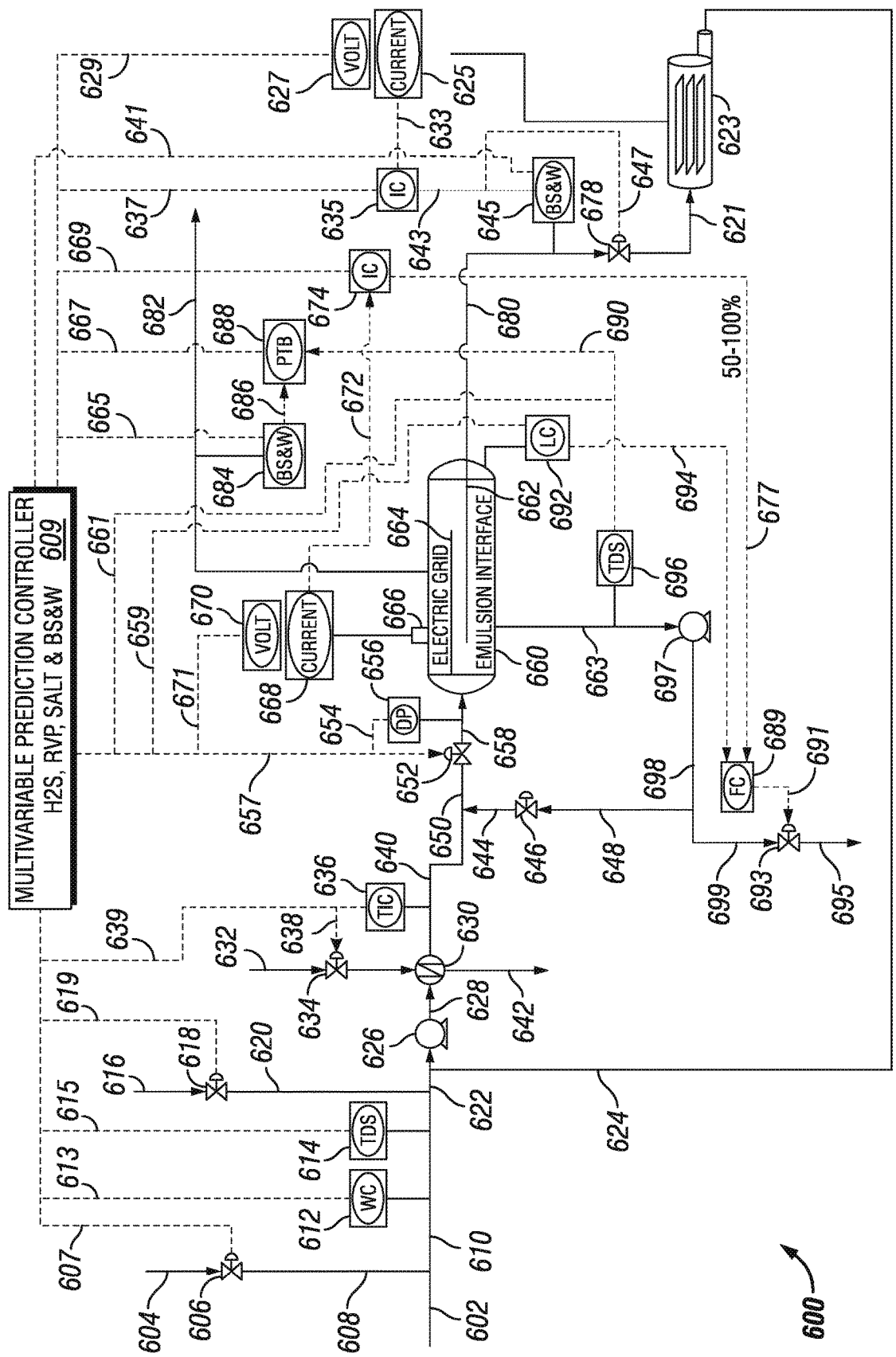
FIG. 6 is a schematic diagram showing an integrated GOSP of the present disclosure with real-time process control using an MPC for controlling salt-in-crude content and water content of produced dry crude oil along with $H_2S$, RVP, and BS&W content, including an inline electrostatic emulsion breaker.

FIG. 6 is a schematic diagram showing an integrated GOSP of the present disclosure with real-time process control using an MPC for controlling salt-in-crude content of produced dry crude oil along with $H_2S$, RVP, and BS&W content, including an inline electrostatic emulsion breaker. Desalter transformer electric current control (measured amps) allows for emulsion interface level control. In GOSP system and process 600, inlet wet crude oil at stream 602 enters and is mixed with one or more, optional, chemical demulsifiers provided via demulsifier stream 604, control valve 606, and demulsifier stream 608. Multivariable prediction controller (MPC) 609 controls valve 606 via signal 607 to increase or decrease the amount of demulsifier as needed, for example to reach the set variables of GOSP system and process 600, such as a maximum PTB salt and maximum volume percent of water in dried, desalted crude oil at the system and process outlet. Mixed wet crude oil and optional chemical demulsifier proceeds via stream 610 to be mixed with wash water (fresh in addition to or alternative to recycle) from wash water inlet stream 616, control valve 618, and wash water inlet stream 620. At stream 610, in the embodiment shown for example, water cut (volume percent water of the mixed feed) is measured via water cut meter 612 and total dissolved solids is measured via TDS meter 614. Signal 613 provides data from water cut meter 612 to MPC 609, and signal 615 provides data from TDS meter 614 to MPC 609. Signal 619 from MPC 409 can control the amount of wash water added to the inlet oil feed via control of valve 618. For example, for higher salinity oils from a hydrocarbon bearing reservoir, identified at TDS meter 614, additional wash water can be signaled to be added at control valve 618 via signal 619 from MPC 609. Signals of the present disclosure can be transmitted both through wired and wireless communications. Signals can be one-way or two-ways between meters, controllers, and MPC's.

Mixed wet crude oil, optional demulsifier, and wash water in stream 622 is next mixed with emulsion recycle from stream 624 and control valve 678 and proceeds to crude charge pump 626 to be pumped via stream 628 to trim heater 630 for heating. A temperature indicating control (TIC) 636 measures, monitors, and controls the desired temperature of stream 640 via signals 638 and 639 to control valve 634, which itself controls inlet heating stream 632 to trim heater 630, and cooled fluid proceeds out of trim heater 630 via stream 642. Trim heater 630 can include any one of or any combination of indirect heat exchangers known in the art, such as shell and tube heat exchangers. Heated mixed oil, optional demulsifier, and wash water in stream 640 is optionally further mixed with recycle water from stream 644 and control valve 646, and proceeds via stream 650 to mixing valve 652. A differential pressure indicator and control 656 at stream 658 controls mixing valve 652 via signals 654 and 657 to ensure efficient mixing of the components in stream 650. For example, if off-spec crude is detected in stream 682, MPC 609 can increase or decrease any one of or any combination of demulsifier injection, wash water injection, trim heating, or mixing at mixing valve 652. An additional pressure gauge (not shown) preceding stream 658 and mixing valve 652, optionally in communication with MPC 609, can help control the differential pressure across mixing valve 652 in combination with differential pressure indicator and control 656.

Mixed stream 658 proceeds into desalter 660 (which in other embodiments could include a separate or integrated dehydrator). Desalter 660 includes an emulsion interface 662, optionally comprising a weir, an electric grid comprising fully insulated electrostatic electrodes 664, and one or more transformer 666 including a current meter 668 and a voltage meter 670. Current meter 668 and voltage meter 670 provide real-time current and voltage data, respectively, to MPC 609 via signal 671.

As shown in FIG. 6, water separating to the bottom of desalter 660 exits via stream 663, and TDS meter 696 measures in real-time TDS in the water, providing the data via signal 690 to PTB controller 688. Dried, desalted crude oil for export, or further stabilization if needed, exits desalter 660 via stream 682 where BS&W meter 684 measures in real-time the BS&W content of stream 682, mostly to determine the water content of the dried, desalted crude oil. BS&W meter 684 sends the measurements in real-time via signal 686 to PTB controller 688. PTB controller 688, using online, real-time readings from TDS meter 696 and BS&W meter 684 calculates in real-time, monitors, and controls in real-time the PTB salt and/or water content in stream 682, in addition to or alternative to MPC 609, such that the dried, desalted crude oil meets set specifications, such as for example less than about 10 PTB and less than about 0.2 volume percent water. PTB controller 688 applies, for example, Equation 1 to calculate the PTB from BS&W and TDS measurements. TDS meter 696, BS&W meter 684, and PTB controller 688 in the embodiment shown are in wired in addition to or alternative to wireless communication with MPC 609 via signals 661, 665, and 667, respectively.

Current meter 668 and a voltage meter 670 of desalter 660 provide signal 672 to current controller 674 for control of flow controller 689 via signal 677. Current controller 674 also exchanges data with MPC 609 via signal 669. When current supplied to one or more transformer 666 is between about 0% and 50% of an acceptable, set maximum current value (for example set by the desalter vendor), the current controller 674 keeps closed drain valve 693 via signal 677 to flow controller 689 and via signal 691 to drain valve 693. In the embodiment of FIG. 6, the emulsion in stream 680 proceeds under normal operation between 0% and 50% of an acceptable, set maximum current value through valve 678 and stream 621 to inline emulsion breaker with insulated electrostatic electrodes 623. Current meter 625 and voltage meter 627 of inline emulsion breaker with insulated electrostatic electrodes 623 provide via signal 633 data to current controller 635 regarding voltage and current supplied to inline emulsion breaker with insulated electrostatic electrodes 623. Inline emulsion breaker with insulated electrostatic electrodes 623, for example a 6" spool of pipe with insulated electrostatic electrodes, optionally placed horizontally or vertically, helps break emulsions such as tight emulsions. Current meter 625 and voltage meter 627 of inline emulsion breaker with insulated electrostatic electrodes 623 also exchange data with MPC 609 via signal 629, and current controller 635 exchanges data with MPC 609 via signal 637.

When current supplied to inline emulsion breaker with insulated electrostatic electrodes 623 is between about 50% and 100% of an acceptable, set maximum current value, control valve 678 can be closed via signals 633, 643, and/or 647 to prevent short circuiting of inline emulsion breaker with insulated electrostatic electrodes 623. BS&W analyzer 645 is installed to measure the volume percent of water inside the withdrawn emulsion layer, and is in communication with MPC 609 via signal 641. BS&W analyzer 645 is used to manipulate the flow of the withdrawn emulsion from between about 1 to 30 gpm. Electric current measured at current meter 625 can be utilized to control and override BS&W analyzer 645 to increase or decrease the flow of the recycled emulsion.

The BS&W readings can be inferred directly from the current. Greater BS&W readings (greater conductivity due to water) signifies a greater current. Typically, BS&W analyzer 645 will control the flow, but if the current meter 625 starts to detect increased current, then additional flow is withdrawn by opening valve 678 to avoid water/emulsion reaching the electric grid 664 in the main desalter 660.

Current meter 625 and current controller 635 are cascaded to BS&W analyzer 645. Current controller 635 is the master controller and BS&W analyzer 645 comprises a slave controller. One objective is to prevent water or emulsion encroaching into the main electric grid 664 in the main desalter 660 by quickly withdrawing the emulsion layer to treat it inside inline emulsion breaker with insulated electrostatic electrodes 623.

When current supplied to one or more transformer 666 is between 50% and 100% of an acceptable, set maximum current value (for example set by the desalter vendor or user), the current controller 674, in addition to or alternative to MPC 609, signals via signal 677 flow controller 689 to open drain valve 693 by signal 691. Control valve 678 can be opened, partially-opened, or closed by signal 647 when drain valve 693 is opened, depending on readings from current meter 625 and voltage meter 627 to current controller 635 by signal 633. Level controller 692 also provides data to flow controller 689 via signal 694 regarding the level of water and/or emulsion in desalter 660. In normal operation between 0% and 50% of an acceptable, set maximum current value, water exiting desalter 660 at stream 663 can be recycled to stream 640 via stream 663, pump 697, stream 698, stream 648, control valve 646, and stream 644. Control valve 646 can be opened, partially-opened, or closed when drain valve 693 is opened. Between 50% and 100% of an acceptable, set maximum current value (for either or both desalter 660 and/or to inline emulsion breaker with insulated electrostatic electrodes 623) and/or at a higher than acceptable emulsion level or water level based on level controller 692, flow controller 689 opens drain valve 693 via signal 691 to allow excess water and/or emulsion to flow out of the system via lines 699 and 695, for example to a WOSEP.

In the embodiments shown, certain units are in one-way or two-way communication with an MPC exchanging data therebetween, and in other embodiments additional or fewer units could be in communication with an MPC, for example control valve 646 or similar valves and units displayed throughout the figures.

Figure 7:
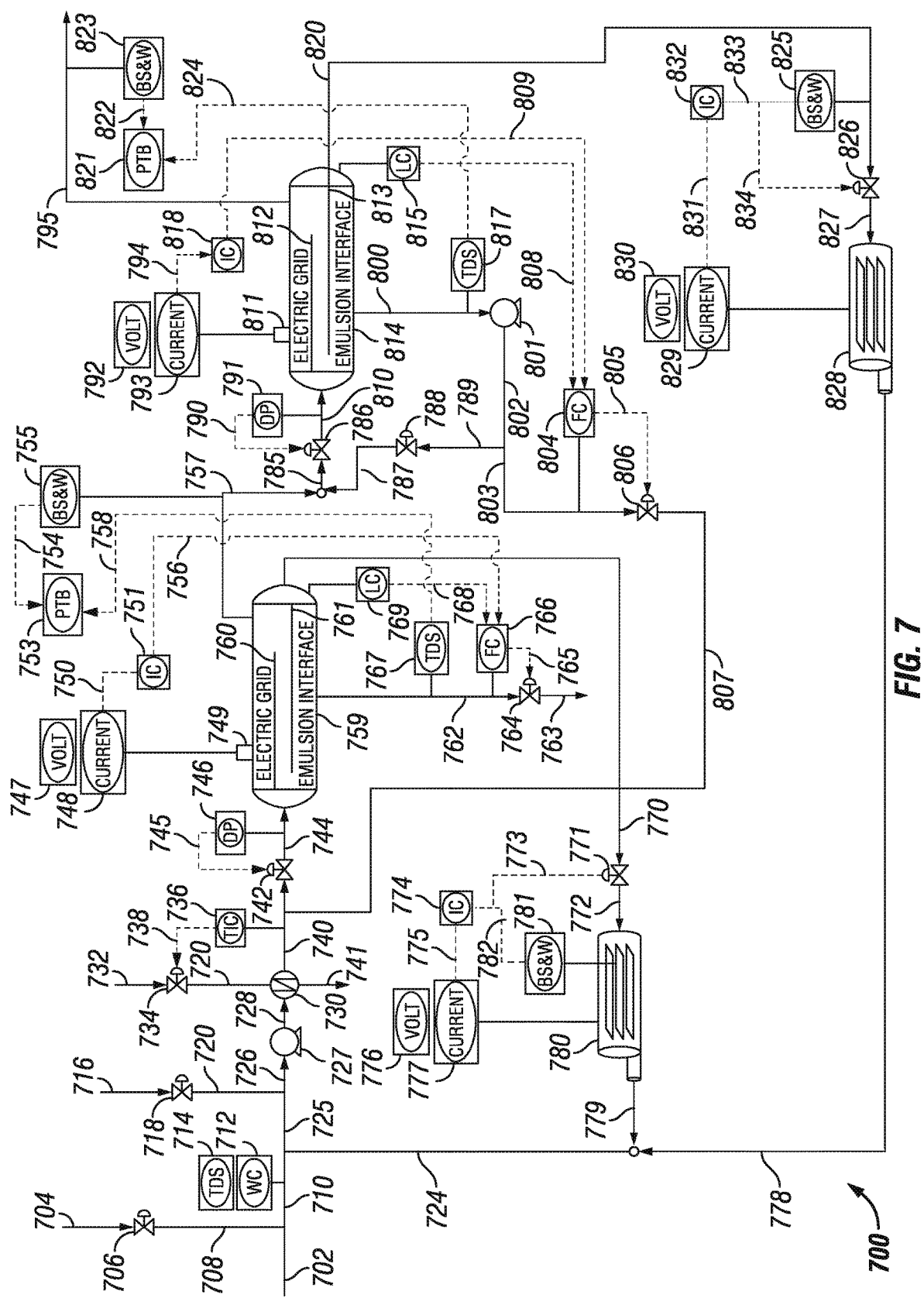
FIG. 7 is a schematic diagram showing an integrated GOSP of the present disclosure with real-time process control for controlling salt-in-crude content and water content of produced dry crude oil, including two inline electrostatic emulsion breakers and two separate separation vessels with fully insulated electrostatic electrodes.

FIG. 7 is a schematic diagram showing an integrated GOSP of the present disclosure with real-time process control for controlling salt-in-crude content of produced dry crude oil, including an inline electrostatic emulsion breaker and 2 separate separation vessels with fully insulated electrostatic electrodes. In other embodiments, the 2-stage desalting system and process of FIG. 7 can integrate MPC control of one or more units. Desalter transformer electric current control (measured amps) allows for emulsion interface level control. In GOSP system and process 700, inlet wet crude oil at stream 702 enters and is mixed with one or more, optional, chemical demulsifiers provided via demulsifier stream 704, control valve 706, and demulsifier stream 708. A multivariable prediction controller (MPC) (not pictured) can control valve 706 via a signal to increase or decrease the amount of demulsifier as needed, for example to reach the set variables of GOSP system and process 700, such as a maximum PTB salt and maximum volume percent of water in dried, desalted crude oil at the system and process outlet.

Mixed wet crude oil and optional chemical demulsifier proceeds via stream 710 to be mixed with wash water (fresh in addition to or alternative to recycle) from wash water inlet stream 716, control valve 718, and wash water inlet stream 720. At stream 710, in the embodiment shown for example, water cut (volume percent water of the mixed feed) is measured via water cut meter 712 and total dissolved solids is measured via TDS meter 714. A signal can provide data from water cut meter 712 to an MPC, and a signal can provide data from TDS meter 714 to an MPC (not pictured). An MPC can control the amount of wash water added to the inlet oil feed via control of valve 718. For example, for higher salinity oils from a hydrocarbon bearing reservoir, identified at TDS meter 714, additional wash water can be signaled to be added at control valve 718 from an MPC. Signals of the present disclosure can be transmitted both through wired and wireless communications. Signals can be one-way or two-ways between meters, controllers, and MPC's.

Stream 710, with optional chemical demulsifier, can also be mixed with recycled, broken oil-water emulsions from streams 724 and stream 778 to form stream 725.

Mixed wet crude oil, optional demulsifier, optional recycled, broken oil-water emulsions, and wash water in stream 726 proceeds to crude charge pump 727 to be pumped via stream 728 to trim heater 730 for heating. A temperature indicating control (TIC) 736 measures, monitors, and controls the desired temperature of stream 740 via signal 738 to control valve 734, which itself controls inlet heating stream 732 to trim heater 730, and cooled fluid proceeds out of trim heater 730 via stream 741. Trim heater 730 can include any one of or any combination of indirect heat exchangers known in the art, such as shell and tube heat exchangers.

Heated mixed oil, optional demulsifier, optional recycled, broken oil-water emulsions, and wash water in stream 740 is optionally further mixed with recycle water from stream 807 and drain valve 806, and proceeds to mixing valve 742. A differential pressure indicator and control 746 at stream 744 controls mixing valve 742 via signal 745 to ensure efficient mixing of the components from streams 740 and 807. For example, if off-spec crude is detected in stream 795, various controllers and/or an MPC can increase or decrease any one of or any combination of demulsifier injection, wash water injection, trim heating, or mixing at mixing valve 742. An additional pressure gauge (not shown) preceding stream 744 and mixing valve 742, optionally in communication with an MPC, can help control the differential pressure across mixing valve 742 in combination with differential pressure indicator and control 746.

Mixed stream 744 proceeds into desalter 759 (which in other embodiments could include a separate or integrated dehydrator). Desalter 759 includes an emulsion interface 761, optionally comprising a weir, an electric grid comprising fully insulated electrostatic electrodes 760, and one or more transformer 749 including a current meter 748 and a voltage meter 747. Current meter 748 and voltage meter 747 provide, in some other embodiments, real-time current and voltage data, respectively, to an MPC.

As shown in FIG. 7, water separating to the bottom of desalter 759 exits via stream 762, and TDS meter 767 measures in real-time TDS in the water, providing the data via signal 758 to PTB controller 753. First-stage dried, desalted crude oil exits desalter 759 via stream 757 where BS&W meter 755 measures in real-time the BS&W content of stream 757, mostly to determine the water content of the dried, desalted crude oil. BS&W meter 755 sends the measurements in real-time via signal 754 to PTB controller 753. PTB controller 753, using online, real-time readings from TDS meter 767 and BS&W meter 755 calculates in real-time, monitors, and controls in real-time the PTB and/or water content in stream 757, in addition to or alternative to an MPC, such that the first-stage dried, desalted crude oil meets set specifications, such as for example less than about 10 PTB salt and less than about 0.2 or 0.3 volume percent water, or less than about 50 PTB and less than about 5 volume percent water. PTB controller 753 applies, for example, Equation 1 to calculate the PTB from BS&W and TDS measurements.

Current meter 748 and voltage meter 747 of desalter 759 provide signal 750 to current controller 751 for control of flow controller 766 via signal 756. Current controller 751 can also exchange data with an MPC in other embodiments. When current supplied to one or more transformer 749 is between about 0% and 50% of an acceptable, set maximum current value (for example set by the desalter vendor), the current controller 751 keeps closed drain valve 764 via signal 756 to flow controller 766 and via signal 765 to drain valve 764. In the embodiment of FIG. 7, the emulsion in stream 770 proceeds under normal operation between 0% and 50% of an acceptable, set maximum current value through valve 771 and stream 772 to inline emulsion breaker with insulated electrostatic electrodes 780. Current meter 777 and voltage meter 776 of inline emulsion breaker with insulated electrostatic electrodes 780 provide via signal 775 data to current controller 774 regarding voltage and current supplied to inline emulsion breaker with insulated electrostatic electrodes 780. Inline emulsion breaker with insulated electrostatic electrodes 780, for example a 6" spool of pipe with insulated electrostatic electrodes, optionally placed horizontally or vertically, helps break emulsions such as tight emulsions. Current meter 777 and voltage meter 776 of inline emulsion breaker with insulated electrostatic electrodes 780 can also exchange data with an MPC in some embodiments.

When current supplied to inline emulsion breaker with insulated electrostatic electrodes 780 is between 50% and 100% of an acceptable, set maximum current value, control valve 771 can be closed via signal 773 to prevent short circuiting of inline emulsion breaker with insulated electrostatic electrodes 780. BS&W analyzer 781 is installed to measure the volume percent of water inside the withdrawn emulsion layer in stream 770. BS&W analyzer 781 is used to manipulate the flow of the withdrawn emulsion from between about 1 to 30 gpm. Electric current measured at current meter 777 can be utilized to control and override BS&W analyzer 781 to increase or decrease the flow of the recycled emulsion.

BS&W readings can be inferred directly from current. Greater BS&W readings (greater conductivity due to water), signifies a greater current. Under normal operation, BS&W analyzer 781 will control flow at valve 771, but if the current at current meter 777 begins to increase, then more flow needs to be withdrawn by opening valve 771 to avoid water/emulsion reaching the electric grid 760 in the main desalter 759.

Current meter 777 and current controller 774 are cascaded to BS&W analyzer 781. Current controller 774 is the master controller and BS&W analyzer 781 comprises a slave controller. One objective is to prevent water or emulsion encroaching into the main electric grid in the main desalter 759 by quickly withdrawing the emulsion layer to treat it inside the inline emulsion breaker with insulated electrostatic electrodes 780.

When current supplied to one or more transformer 749, and/or inline emulsion breaker with insulated electrostatic electrodes 780, is between 50% and 100% of an acceptable, set maximum current value (for example set by the desalter vendor or user), the current controller 751, in addition to or alternative to an MPC, signals via signal 756 flow controller 766 to open drain valve 764 by signal 765. Control valve 771 can be opened, partially-opened, or closed by signal 773 when drain valve 764 is opened, depending on readings from current meter 777 and voltage meter 776 to current controller 774 by signal 775. Level controller 769 also provides data to flow controller 766 via signal 768 regarding the level of water and/or emulsion in desalter 759. In normal operation between 0% and 50% of an acceptable, set maximum current value, water exiting desalter 759 at stream 762 can be recycled to stream 710 via stream 770 (not pictured). Between 50% and 100% of an acceptable, set maximum current value (for either or both desalter 759 and/or to inline emulsion breaker with insulated electrostatic electrodes 780) and/or at a higher than acceptable emulsion level or water level based on level controller 769, flow controller 766 opens drain valve 764 via signal 765 to allow excess water and/or emulsion to flow out of the system via streams 762 and 763, for example to a WOSEP. Recycled, broken emulsions are recycled to stream 710 via stream 724.

Stream 757 from desalter 759 proceeds to desalter 814 in a second stage. Stream 757 is optionally mixed with a recycle water stream 787. A differential pressure indicator and control 791 at stream 785 controls mixing valve 786 via signal 790 to ensure efficient mixing of the components from streams 757 and 787. For example, if off-spec crude is detected in stream 795, various controllers and/or an MPC can increase or decrease any one of or any combination of demulsifier injection, wash water injection, trim heating, emulsion recycle, water draining, or mixing at mixing valves 742 and 786. An additional pressure gauge (not shown) preceding stream 810 and mixing valve 786, optionally in communication with an MPC, can help control the differential pressure across mixing valve 786 in combination with differential pressure indicator and control 791. Mixed stream 810 proceeds into desalter 814 (which in other embodiments could include a separate dehydrator). Desalter 814 includes an emulsion interface 813, optionally comprising a weir, an electric grid comprising fully insulated electrostatic electrodes 812, and one or more transformer 811 including a current meter 793 and a voltage meter 792. Current meter 793 and voltage meter 792 provide, in some other embodiments, real-time current and voltage data, respectively, to an MPC.

As shown in FIG. 7, water separating to the bottom of desalter 814 exits via stream 800, and TDS meter 817 measures in real-time TDS in the water, providing the data via signal 824 to PTB controller 821. Second-stage dried, desalted crude oil exits desalter 814 via stream 795 where BS&W meter 823 measures in real-time the BS&W content of stream 795, mostly to determine the water content of the dried, desalted crude oil. BS&W meter 823 sends the measurements in real-time via signal 822 to PTB controller 821. PTB controller 821, using online, real-time readings from TDS meter 817 and BS&W meter 823 calculates in real-time, monitors, and controls in real-time the PTB and/or water content in stream 795, in addition to or alternative to an MPC, such that the second-stage dried, desalted crude oil meets set specifications, such as for example less than about 10 PTB salt and less than about 0.2 volume percent water. PTB controller 821 applies, for example, Equation 1 to calculate the PTB from BS&W and TDS measurements.

Current meter 793 and voltage meter 792 of desalter 814 provide signal 794 to current controller 818 for control of flow controller 804 via signal 809. Current controller 818 can also exchange data with an MPC in other embodiments. When current supplied to one or more transformer 811 is between 0% and 50% of an acceptable, set maximum current value (for example set by the desalter vendor), the current controller 818 keeps closed drain valve 806 via signal 809 to flow controller 804 and via signal 805 to drain valve 806. In the embodiment of FIG. 7, the emulsion in stream 820 proceeds under normal operation between 0% and 50% of an acceptable, set maximum current value through control valve 826 and stream 827 to inline emulsion breaker with insulated electrostatic electrodes 828. Current meter 829 and voltage meter 830 of inline emulsion breaker with insulated electrostatic electrodes 828 provide via signal 831 data to current controller 832 regarding voltage and current supplied to inline emulsion breaker with insulated electrostatic electrodes 828. Inline emulsion breaker with insulated electrostatic electrodes 828, for example a 6" spool of pipe with insulated electrostatic electrodes, optionally placed horizontally or vertically, helps break emulsions such as tight emulsions. Current meter 829 and voltage meter 830 of inline emulsion breaker with insulated electrostatic electrodes 828 can also exchange data with an MPC in some embodiments.

When current supplied to inline emulsion breaker with insulated electrostatic electrodes 828 is between about 50% and 100% of an acceptable, set maximum current value, control valve 826 can be closed via signals 833 and 834 to prevent short circuiting of inline emulsion breaker with insulated electrostatic electrodes 828. BS&W analyzer 825 is installed to measure the volume percent of water inside the withdrawn emulsion layer in stream 820. BS&W analyzer 825 is used to manipulate the flow of the withdrawn emulsion from between about 1 to 30 gpm. Electric current measured at current meter 829 can be utilized to control and override BS&W analyzer 825 to increase or decrease the flow of the recycled emulsion.

BS&W readings can be inferred directly from current. Greater BS&W readings (greater conductivity due to water), signifies a greater current. Under normal operation, BS&W analyzer 825 will control flow at valve 826, but if the current at current meter 829 begins to increase, then more flow needs to be withdrawn by opening valve 826 to avoid water/emulsion reaching the electric grid 812 in the main desalter 814.

Current meter 829 and current controller 832 are cascaded to BS&W analyzer 825. Current controller 832 is the master controller and BS&W analyzer 825 comprises a slave controller. One objective is to prevent water or emulsion encroaching into the main electric grid in the main desalter 814 by quickly withdrawing the emulsion layer to treat it inside the inline emulsion breaker with insulated electrostatic electrodes 828.

When current supplied to one or more transformer 811, and/or inline emulsion breaker with insulated electrostatic electrodes 828, is between 50% and 100% of an acceptable, set maximum current value (for example set by the desalter vendor or user), the current controller 818, in addition to or alternative to an MPC, signals via signal 809 flow controller 804 to open drain valve 806 by signal 805. Control valve 826 can be opened, partially-opened, or closed by signal 834 when drain valve 806 is opened, depending on readings from current meter 829 and voltage meter 830 to current controller 832 by signal 831. Level controller 815 also provides data to flow controller 804 via signal 808 regarding the level of water and/or emulsion in desalter 814. In normal operation between 0% and 50% of an acceptable, set maximum current value, water exiting desalter 814 at stream 800 can be recycled to stream 785 via pump 801, stream 802, stream 789, control valve 788, and stream 787. Between 50% and 100% of an acceptable, set maximum current value (for either or both desalter 814 and/or to inline emulsion breaker with insulated electrostatic electrodes 828) and/or at a higher than acceptable emulsion level or water level based on level controller 815, flow controller 804 opens drain valve 806 via signal 805 to allow excess water and/or emulsion to flow out of the system via streams 803 and 807 to be recycled to desalter 759 in the first stage. Broken emulsion from inline emulsion breaker with insulated electrostatic electrodes 828 proceeds via stream 778 for recycle in the first stage.

In some embodiments, hydrogen, nitrogen, steam, and/or other stripping gasses are applied to meet an $H_2S$ crude specifications of 10 ppm, optionally using a crude oil stabilizer with 16 actual trays along with steam injection.

In embodiments disclosed here, when fresh wash water is applied in addition to or alternative to recycle wash water, a suitable volume/volume ratio for water to crude oil and hydrocarbons is between about 1 V % to about 9 V %. A lesser V/V wash water to oil and hydrocarbons is used when the salt content is less than 1,000 ppm. With greater salt content in wash water, a greater volume is used. For example, V/V for recycle water as wash water to crude oil and hydrocarbons is between about 4 V % or 5 V % to about 9 V %.

Heat exchangers, such as trim heat exchangers, can include any one of or any combination of indirect heat exchangers such as shell and tube heat exchangers. Desalted, dried crude oil for shipment in some embodiments meets specifications including the following: (1) a salt concentration of not more than about 10 PTB; (2) BS&W of not more than about 0.3 V %; (3) $H_2S$ content of less than about 60 ppm in the crude stabilization tower (or degassing vessels in the case of sweet crude); and (4) a maximum RVP of about 7 psia and a maximum TVP of about 13.5 psia at 130° F.

Prior art GOSP systems also suffer from the following issues: transformer tripping and inefficient energy usage; off-specification crude oil production in terms of BS&W and salt content; high operating costs required to meet the crude specifications; and inefficient human and manual operations.

Certain prior art treatments are limited to treating crude oil with a low water cut (approximately 30% by volume), while water cut in certain emulsion layers can reach as high as about 85% for tight emulsions in heavy crude oil applications. Suitable insulated electrostatic electrodes are capable of handling up to 100% water cut herein without short circuiting, and this enhances the emulsion breaking capabilities of separation vessels. Limiting and treating the emulsion rag layer will avoid off-specification crude oil products and minimize demulsifier and wash water consumption. In embodiments of the disclosure, systems and methods enable the efficient control, reduction, in addition to or alternative to elimination of the rag layer. Embodiments of the disclosure can separate up to about 90% of the water content in the rag layer depending on operating temperature, crude type, electrostatic coalescers and demulsifier used, or alternatively up to about or greater than about 95% of the water content in the rag layer.

The emulsion layer can consist of water, oil, and solids. Subjecting the emulsion layer to high voltage electric fields will result in water droplets being distorted into an elliptical shape, with positive charges accumulating at the end nearest the negative electrode of the external electric field, and negative charges at the end nearest the positive electrode. The drops become induced dipoles. Two adjacent droplets in the field will have an electrical attraction for one another. The negative end of one droplet is nearest the positive end of the neighboring droplet, so there is an attractive force between the two that tends to draw them together. This force is of sufficient magnitude to rupture the interfacial film between the droplets upon collision, and allows them to coalesce into one larger droplet. The resulting larger water droplets (globules), along with water-insoluble solids, settle to the bottom of a vessel or pipe.

For purposes of the present disclosure, tight emulsion crude oil includes emulsions that occur in medium to heavy crude oils with American Petroleum Institute (API) numbers less than about 29. Crude oil specific gravity, along with API numbers, can be used as a measure of crude oil quality. Higher API values indicate lighter oils and, thus, a higher market value. Water cut in oil production refers to the total volume of water in the crude oil stream divided by the total volume of crude oil and water, or water cut percent=total volumetric flowrate of water/(volumetric flowrate of water+volumetric flowrate of crude oil)*100. Water cut increases with oil and gas well age during continuous production of oil and gas wells. Water cut at the beginning of the well life can be around zero percent and can reach close to 100% by the end of the life of the well. "Wet" crude oil normally has more than about 0.3 volume percent of water while "dry" crude has less than 0.3 volume percent water.

Insulated electrostatic electrodes can be similar to those of Wartsila Corporation of Helsinki, Finland produced under the term Vessel Internal Electrostatic Coalescers (VIEC). Another supplier of suitable electrodes would include Cameron International Corporation (a Schlumberger Company) of Houston, Texas. Emulsion separation vessel technology described in U.S. Pat. No. 10,513,663 is suitable in certain embodiments of the present disclosure and is incorporated here by reference in its entirety. Fully-insulated electrostatic electrodes are capable of handling up to 100% water cut, and the electrodes can be fully deactivated at about 100% water cut.

Typically, wash water salinity ranges from about 100 ppm to about 12,000 ppm salt in embodiments of the present disclosure. Wash water will be more effective at lower salinity. Formation water salinity inside crude oil can reach as high as 270,000 ppm of salt content. Demulsifiers, or emulsion breakers, are chemicals used to separate emulsions (for example oil-in-water emulsions). Some commercially available demulsifiers are Petrolite DMO-22241 by Baker Petrolite, Emulsotron CC-8948 by Champion Technologies, SUGEST 9005 by German Metal Surface Treatment Chemical Co., Clariant Phasetreat 4688 by Clariant, or any other suitable demulsifier.

A desalter operating pressure can be greater than about 35 psig, depending on the vapor pressure of the fluid inside the desalter. Crude oil fed to a desalter is required to be below its bubble point to ensure no free vapor is liberated in the process. Desalters are designed to be 'gas free,' since the presence of vapor in a high voltage field can cause arcing which in turn leads to more vapor formation. Desalters can operate at about 25 psig higher than the fluid vapor pressure to avoid vaporization inside the desalters and potential arcing.

In integrated GOSP systems and processes of the present disclosure, a wet and unstabilized crude oil from oil production wells, either or both onshore or offshore, for example at about 63° F., or between about 40° F. and 80° F., enters through an inlet.

Some embodiments of desalters can include one or more cyclonic separator, for example at the inlet, to separate components of a mixed inlet stream.

The plurality of fully-insulated electrostatic electrodes can simultaneously dehydrate crude oil and remove emulsified water, for example up to 98% of emulsified water. Fresh wash water can be used in the desalting processes to ensure that the maximum amount of salt is rinsed from the crude oil. Injecting low salinity water before heat exchangers aids in minimizing fouling.

Heating crude makes it easier to separate out gas and enhance the desalting efficiency. Electrostatic coalescence removes the remaining water emulsion from the crude oil eliminating the need for $2^{nd}$ stage desalters, in some embodiments.

Wet crude oil generally contains some free salty water, and salty water in the form of an emulsion. The emulsion is separated into layers of oil and water by electrostatic coalescence. Electrostatic coalescence applies an electric current, causing water droplets in an emulsion to collide, coalesce into larger (heavier) drops, and settle out of the crude oil as separate liquid water. This process partially dries wet crude oil.

Stabilization is a process carried out using heating to remove any remaining dissolved gases, light, volatile hydrocarbons, and $H_2S$. Crude oil is hence split into two components: atmospheric gas from the overhead, and stabilized, sweetened crude oil from the bottoms, for example at a cold stabilizer product bottom stream. Stabilizing crude oil is achieved when crude oil is heated in a multiple stages of separation drums working at increasing temperatures and reduced pressure.

A cold stabilizer performs two functions simultaneously by sweetening sour crude oil by removing the hydrogen sulfide, and reducing the vapor pressure through removal of light, volatile hydrocarbons, thereby making the crude oil safe for shipment in pipelines. Stabilization involves the removal of light ends from crude oil, mainly $C_1$-$C_4$ hydrocarbons, to reduce the vapor pressure to produce dead or stable product that can be stored in an atmospheric tank. Stabilization aims to lower vapor pressure of crude oil to a maximum RVP of about 7 psia and a maximum TVP of about 13.5 psia at 130° F., or in other words low enough so no vapor will flash under atmospheric conditions, making it safe for transportation and shipment. Operating conditions of a stabilizer, such as for example a cold stabilizer, include temperature in a range from about 160° F. to about 200° F. and pressure from about 3 psig to about 5 psig.

In some applications in Saudi Arabia, crude oil grade is measured by the American Petroleum Institute (API) range as follows: Arabian Super Light (49-52 API); Arabian Extra Light (37-41 API); and Arabian Light (32-36 API). API=141.5/(crude oil specific gravity)—131.5.

Wet crude oil as used in the specification generally refers to crude oil having more than about 0.3 volume percent of water, while dry crude oil has less than about 0.3 volume percent of water. The phrase lighter hydrocarbons as used throughout the specification refers generally to $C_{1-4}$ components such as, for example, methane, ethane, propane, butane, iso-butane, and trace amounts of $C_{5+}$ compounds. The phrase heavier hydrocarbons as used in the specification refers generally to $C_{5+}$ or five-carbon and greater hydrocarbons such as, for example, pentane, is-pentane, hexane, and heptane. Heavier hydrocarbons can have trace amounts of lighter hydrocarbons.

Operating conditions of a desalter such as desalter can include a temperature range from about 130° F. to about 160° F. and a pressure at about 25 psig above the crude vapor pressure.

Second stage desalters are not required in certain embodiments of the present disclosure. Sweetening involves the removal of dissolved $H_2S$ gas from crude oil to meet specifications in a range of about 10-60 ppm $H_2S$. Sweetening is performed to reduce corrosion to pipelines and eliminate health and safety hazards associated with $H_2S$. Steam can be used to strip $H_2S$ gas from crude oil in addition to or alternative to any other suitable stripping gas that is low in $H_2S$ concentration relative to the crude oil. Suitable stripping gas streams include natural gas low in $H_2S$ concentration (such as methane and ethane), steam, and nitrogen ($N_2$).

Demulsifiers enhance desalting processes and allow treatment of "tight" emulsions. Also referred to as emulsion breakers, demulsifiers are chemicals used to separate emulsions such as, for example, water in oil. For example, one such demulsifier is PHASETREAT® by Clariant of Muttenz, Switzerland.

Efficient inlet mixing devices and cyclonic separators can improve the separation of gas and liquid in vessels such as a desalter, or in separation vessels preceding a desalter.

Inline gas separators include compact gas/liquid separators that apply cyclonic separation techniques to generate high gravitational forces ("G-Forces") with a low pressure drop to achieve high separation performance of gas from liquid in a pipe spool. Inline separators can be considered as one equilibrium separation stage, and produce very high quality separate gas and liquid streams.

Although the disclosure has been described with respect to certain features, it should be understood that the features and embodiments of the features can be combined with other features and embodiments of those features. Certain units not shown such as heat exchangers, compressors, valves, off-gas vents, and other will be understood to apply as needed by those of ordinary skill in the art.

Although the disclosure has been described in detail, it should be understood that various changes, substitutions, and alterations can be made hereupon without departing from the principle and scope of the disclosure. Accordingly, the scope of the present disclosure should be determined by the following claims and their appropriate legal equivalents.

The singular forms "a," "an," and "the" include plural referents, unless the context clearly dictates otherwise. The term "about" in some embodiments includes values 5% above or below the value or range of values provided.

As used throughout the disclosure and in the appended claims, the words "comprise," "has," and "include" and all grammatical variations thereof are each intended to have an open, non-limiting meaning that does not exclude additional elements or steps.

As used throughout the disclosure, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present disclosure.

While the disclosure has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present disclosure may suitably comprise, consist or consist essentially of the elements disclosed and may be practiced in the absence of an element not disclosed.

What is claimed is:

1. A system for controlling desalting and dehydration of crude oil, the system comprising:
    a crude oil separation unit, the crude oil separation unit comprising a crude oil inlet, insulated electrostatic electrodes, a water outlet, an oil-water emulsion outlet, and a dried, desalted crude oil product outlet;
    a total dissolved solids (TDS) content monitor at the water outlet;
    a basic sediment and water (BS&W) content monitor at the dried, desalted crude oil product outlet; and
    a pounds per thousand barrels (PTB) salt content and volumetric water content controller in electronic communication with the TDS content monitor and the BS&W content monitor, wherein the PTB salt content and volumetric water content controller controls a process input to the system based on a comparison between the PTB salt content and volumetric water content of a dried, desalted processed crude oil stream at the dried, desalted crude oil product outlet versus a maximum set value for PTB salt content and volumetric water content of the dried, desalted processed crude oil stream, where the controlled process input is selected from the group consisting of chemical demulsifier injection rate; wash water injection rate; inlet crude oil heating; a pressure drop for mixing preceding the crude oil separation unit; current supply to the crude oil separation unit; inlet crude oil flow rate for processing; outlet crude oil flow rate of the dried, desalted crude oil product outlet; crude oil separation unit residence time; crude oil separation unit emulsion level; crude oil separation unit water level; and combinations thereof.

2. The system according to claim 1, wherein the PTB salt content and volumetric water content controller applies Equation 1 with on-line, real-time TDS measurements from the TDS content monitor and on-line, real-time BS&W measurements from the BS&W content monitor.

3. The system according to claim 1, further comprising a current monitor and a voltage monitor for the insulated electrostatic electrodes, the current monitor and voltage monitor in electronic communication with a current controller, where the current controller is operable to control removal of water via the water outlet and removal of an oil-water emulsion via the oil-water emulsion outlet.

4. The system according to claim 3, the system further comprising a flow controller, the flow controller in electronic communication with the current controller and in electronic communication with a level controller of the crude oil separation unit, the level controller operable to measure a water level or oil-water emulsion level in the crude oil separation unit, and the flow controller operable to control water drained from the system via the water outlet.

5. The system according to claim 4, wherein when electric current supplied to the insulated electrostatic electrodes is at between 0% to about 50% of a set, maximum current value, removal of the oil-water emulsion proximate an oil-water interface of the crude oil separation unit proceeds for recycle of the oil-water emulsion to the crude oil separation unit.

6. The system according to claim 5, wherein when electric current supplied to the insulated electrostatic electrodes is at between about 50% to about 100% of a set, maximum current value, removal of water from the system via a water drain following the water outlet proceeds.

7. The system according to claim 1, wherein the maximum set value for PTB salt content is about 10 PTB and the maximum set value for volumetric water content is about 0.3 volume percent for the dried, desalted crude oil product stream.

8. The system according to claim 1, where the system includes a controller selected from the group consisting of: a distributed control system; a multivariable controller; a multivariable predictive controller; and combinations thereof.

9. The system according to claim 8, where the controller is in one-way or two-way electronic communication with any one of or any combination of a chemical demulsifier injection control valve, a water content monitor for inlet crude oil, a total dissolved solids content monitor for inlet crude oil, a wash water injection control valve, a temperature indicator and control for crude oil inlet heating, a differential pressure indicator and control for control of a mixing valve for inlet crude oil, a current monitor for the insulated electrostatic electrodes, a voltage monitor for the insulated electrostatic electrodes, a level indicator and controller for a water level or oil-water emulsion level in the crude oil separation unit, the TDS content monitor at the water outlet, the BS&W content monitor at the dried, desalted crude oil product outlet, the PTB salt content and volumetric water content controller, a flow controller for draining water at the water outlet, a current controller in electronic communication with the current monitor for the insulated electrostatic electrodes and the voltage monitor for the insulated electrostatic electrodes, a current monitor for an inline electrostatic emulsion breaker, a voltage monitor for the inline electrostatic emulsion breaker, a current controller in electronic communication with the current monitor for the inline electrostatic emulsion breaker and the voltage monitor for the inline electrostatic emulsion breaker, and a BS&W content monitor at the oil-water emulsion outlet.

10. The system according to claim 1, further comprising an inline electrostatic emulsion breaker at the oil-water emulsion outlet, the inline electrostatic emulsion breaker comprising a current monitor and voltage monitor in electronic communication with an inline electrostatic emulsion breaker current controller, the inline electrostatic emulsion breaker current controller operable to control an inlet valve to the inline electrostatic emulsion breaker.

11. The system according to claim 10, wherein when electric current supplied to an electric grid of the inline electrostatic emulsion breaker is at between 0% to about 50% of a set, maximum current value, removal of an oil-water emulsion proximate the oil-water emulsion outlet of the crude oil separation unit proceeds for recycle of the oil-water emulsion to the crude oil separation unit through the inline electrostatic emulsion breaker.

12. The system according to claim 10, wherein when electric current supplied to the electric grid of the inline electrostatic emulsion breaker is at between about 50% to about 100% of a set, maximum current value, removal of water via a water drain of the crude oil separation unit following the water outlet proceeds.

13. The system according to claim 10, further comprising a BS&W content monitor at an inlet of the inline electrostatic emulsion breaker.

14. The system according to claim 1, where the crude oil separation unit comprises a first stage desalter and a second stage desalter.

15. The system according to claim 14, where the first stage desalter recycles an emulsion layer to a first inline electrostatic emulsion breaker and where the second stage desalter recycles an emulsion layer to a second inline electrostatic emulsion breaker.

* * * * *